(12) United States Patent
McMahon et al.

(10) Patent No.: US 7,908,011 B2
(45) Date of Patent: Mar. 15, 2011

(54) VISUAL PROSTHESIS FITTING

(75) Inventors: Matthew J. McMahon, Los Angeles, CA (US); Arup Roy, Santa Clarita, CA (US); Scott Greenwald, Seattle, WA (US); Ione Fine, Seattle, WA (US); Alan Matthew Horsager, Los Angeles, CA (US); Avraham I. Caspi, La Jolla, CA (US); Kelly Hobart McClure, Simi Valley, CA (US); Robert Jay Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 173 days.

(21) Appl. No.: 11/927,258

(22) Filed: Oct. 29, 2007

(65) Prior Publication Data
US 2008/0058897 A1 Mar. 6, 2008

Related U.S. Application Data

(62) Division of application No. 11/796,425, filed on Apr. 27, 2007.

(60) Provisional application No. 60/795,936, filed on Apr. 28, 2006, provisional application No. 60/834,239, filed on Jul. 28, 2006, provisional application No. 60/838,433, filed on Aug. 16, 2006, provisional application No. 60/848,068, filed on Sep. 29, 2006, provisional application No. 60/834,778, filed on Jul. 31, 2006.

(51) Int. Cl.
*A61N 1/08* (2006.01)

(52) U.S. Cl. .................. 607/54; 607/46; 607/53; 607/59

(58) Field of Classification Search ............... 607/46, 607/53, 54, 55–57, 59
See application file for complete search history.

(56) References Cited

U.S. PATENT DOCUMENTS

| | | | |
|---|---|---|---|
| 5,109,844 A | 5/1992 | de Juan, Jr. et al. | |
| 5,935,155 A | 8/1999 | Humayun et al. | |
| 5,944,747 A | 8/1999 | Greenberg et al. | |
| 6,393,325 B1 * | 5/2002 | Mann et al. | 607/46 |
| 6,400,989 B1 | 6/2002 | Eckmiller | |
| 6,458,157 B1 | 10/2002 | Suaning | |
| 6,609,032 B1 * | 8/2003 | Woods et al. | 607/46 |

(Continued)

FOREIGN PATENT DOCUMENTS
WO  WO 96/39221   12/1996
WO  WO 2007/064916 A2   6/2007

OTHER PUBLICATIONS

E.M. Schmidt, et al.; Feasiblity of a Visual Prosthesis for the Blind Based on Intracortical Microstimulation...; Oxford University Press 1996, Brain (1996), 119, 507-522.

(Continued)

*Primary Examiner* — Niketa I Patel
*Assistant Examiner* — Hiba El-Kaissi
(74) *Attorney, Agent, or Firm* — Scott B. Dunbar; Alessandro Steinfl; Tomas Lendvai

(57) ABSTRACT

Methods and devices for fitting a visual prosthesis are described. In one of the methods, threshold levels and maximum levels for the electrodes of the prosthesis are determined and a map of brightness to electrode stimulation levels is later formed. A fitting system for a visual prosthesis is also discussed, together with a computer-operated system having a graphical user interface showing visual prosthesis diagnostic screens and visual prosthesis configuration screens.

9 Claims, 40 Drawing Sheets

U.S. PATENT DOCUMENTS

| | | |
|---|---|---|
| 6,718,209 B2 | 4/2004 | Williamson et al. |
| 6,974,533 B2 | 12/2005 | Zhou |
| 7,386,348 B2 * | 6/2008 | North et al. .................... 607/46 |
| 2004/0152946 A1 * | 8/2004 | Franck ........................... 600/25 |
| 2005/0222624 A1 | 10/2005 | Greenberg et al. |

OTHER PUBLICATIONS

M. Feucht, et al.; Development of an Epiretinal Prosthesis for Stimulation of the Human Retinal; Ophthalmologe 2005—102:688-691 DOI 10.1007/s00347-005-1186-6.

* cited by examiner

FIG. 39

VISUAL PROSTHESIS FITTING

CROSS REFERENCE TO RELATED APPLICATIONS

This application is a divisional of application Ser. No. 11/796,425, filed Apr. 27, 2007 for "Visual Prosthesis Fitting", by Matthew J. Mciviahon, Arup Roy, Scott Greenwald, Ione Fine, Alan M. Horager, Avi I. Caspi, Kelly H. McClure and Robert J. Greenberg, which claims the benefit of U.S. provisional Patent Application No. 60/795,936, filed Apr. 28, 2006 for "Visual Prosthesis Fitting" by Avi I. Caspi, Kelly H. McClure and Robert J. Greenberg, U.S. provisional Patent Application Ser. No. 60/834,239, filed Jul. 28, 2006 for "Visual Prosthesis Configuration and Fitting System" by Robert J. Greenberg, Matthew J. McMahon, Grant Palmer and Kelly H. McClure, U.S. provisional Patent Application Ser. No. 60/838,433, filed Aug. 16, 2006 for "Visual Prosthesis Configuration and Fitting System" by Robert J. Greenberg, Matthew J. McMahon, Grant Palmer and Kelly H. McClure, U.S. provisional Patent Application Ser. No. 60/848,068, filed Sep. 29, 2006 for "Chapter 4: Clinical Fitting & Psychophysical Testing" by Robert J. Greenberg, Kelly H. McClure, Matthew J. McMahon, and Arup Roy, and U.S. provisional Patent Application Ser. No. 60/834,778, filed Jul. 31, 2006 for "System and Method for Spatial Mapping of a Visual Prosthesis" by Avi Caspi, Matthew J. McMahon, and Robert J. Greenberg, the disclosure of all of which is incorporated herein by reference.

FEDERALLY SPONSORED RESEARCH OR DEVELOPMENT

The present invention was made with support from the United States Government under Grant number R24EY12893-1, awarded by the National Institutes of Health. The United States Government has certain rights in the invention.

FIELD

The present disclosure relates to visual prostheses. More particularly, the present disclosure relates to configuring a visual prosthesis implanted in a patient.

BACKGROUND

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular visual prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Opthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a visual prosthesis for use with the flat retinal array described in de Juan.

In outer retinal degeneration, such as retinitis pigmentosa (RP), the photoreceptors and their supporting retinal pigment epithelium are impaired. In RP (incidence 1:4000) legal blindness is reached after 25 years. In many RP patients over sixty years of age, elementary vision with only gross movement or bright light perception remains, with little or no appreciable peripheral vision. Eventually, even light perception may recede. Currently, there is no treatment that stops or reverses the loss of photoreceptors in retinitis pigmentosa.

Traditionally, the approach to vision rehabilitation in subjects with retinitis pigmentosa has been to use the remaining vision with optical aides. If no useful vision is achieved, auditory or tactile information is substituted (e.g. Braille, cane travel, etc.). Attempts to remedy or alleviate vision loss have been made by replacing damaged cells or by electrically stimulating an undamaged proximal level, bypassing impaired cells. Replacement of damaged photoreceptors has been studied in animals through transplantation. Although there are indications that transplanted photoreceptors can make functional connections, many questions remain about the optimal methods to achieve long term graft survival and functionality in a human eye.

More recently, visual prostheses have been developed to address the extreme low vision population with retinal degeneration. Electrical stimulation at the primary visual cortex has been attempted and has the advantage of not requiring a viable optic nerve. However, such cortical stimulation has its own risks, such as exposing the brain to surgical complication and infection.

Stimulation at more distal neuronal locations has received recent attention and may provide an alternative in an outer retinal degenerative disease such as retinitis pigmentosa. Electrical stimulation of the optic nerve has been used to elicit a sensation of streaks or dots (phosphenes). Also, electrical stimulation through a contact lens electrode elicits phosphenes in subjects with advanced photoreceptor degeneration. These perceptual responses, and the electrically evoked responses recorded from the scalp in response to such stimuli, have been interpreted as evidence that inner retinal cells in subjects with photoreceptor degeneration retain at least partial function. However, the phosphenes elicited with a contact lens electrode or by electrical stimulation of the optic nerve lack well defined shape or localization.

The production of a small localized visual percept that might allow the generation of a two-dimensional array of phosphenes to provide "pixelized visual input" has been explored in both acute and chronic studies of blind subjects. Even partial restoration of vision in subjects blind from photoreceptor degeneration has been shown to be important.

SUMMARY

According to a first aspect, a method for fitting a visual prosthesis having a plurality of electrodes is disclosed, the method comprising: determining at least one level on a first electrode by patient feed back; determining at least one other level for subsequent electrodes based on previous results and further patient feedback; and creating and storing a map of brightness to electrode stimulation levels based on the established levels.

According to a second aspect, a method for fitting a visual prosthesis having a plurality of electrodes is disclosed, comprising: providing a video camera associated with a pair of glasses; capturing an image through the video camera; sending the image to a video processing unit; converting the image to a digital image; processing the digital image to obtain a processed digital image; and presenting the processed digital image to the retina of a subject by way of electrical stimulation.

According to a third aspect, a computer-operated system comprising a display component is disclosed, the display component having a graphical user interface associated with a method for fitting a visual prosthesis having a plurality of electrodes, the graphical user interface comprising: a visual prosthesis diagnostic screen; and a visual prosthesis configuration screen.

According to a fourth aspect, a method for providing a direct measurement of individual phosphene locations within a video image is provided, comprising: stimulating a plurality of electrodes, each electrode producing a phosphene when stimulated; asking a subject to locate the phosphenes; and recording a subject's location of the phosphenes in the video image.

According to a fifth aspect, a device for implementing any one of the methods and/or method steps disclosed in the present specification, drawings or claims, is disclosed.

Further embodiments are shown in the specification, drawings and claims of the present application.

BRIEF DESCRIPTION OF THE FIGURES

FIG. 39 shows a 'Brightness Matching' computer screen.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

The present disclosure provides a method of fitting, configuring and optimizing a visual prosthesis (i.e. device) for an individual patient (i.e. subject) including creating a map of brightness to electrical stimulation levels for each electrode, and using that map for the stimulation of retinal neurons to create artificial vision.

Figure 1:
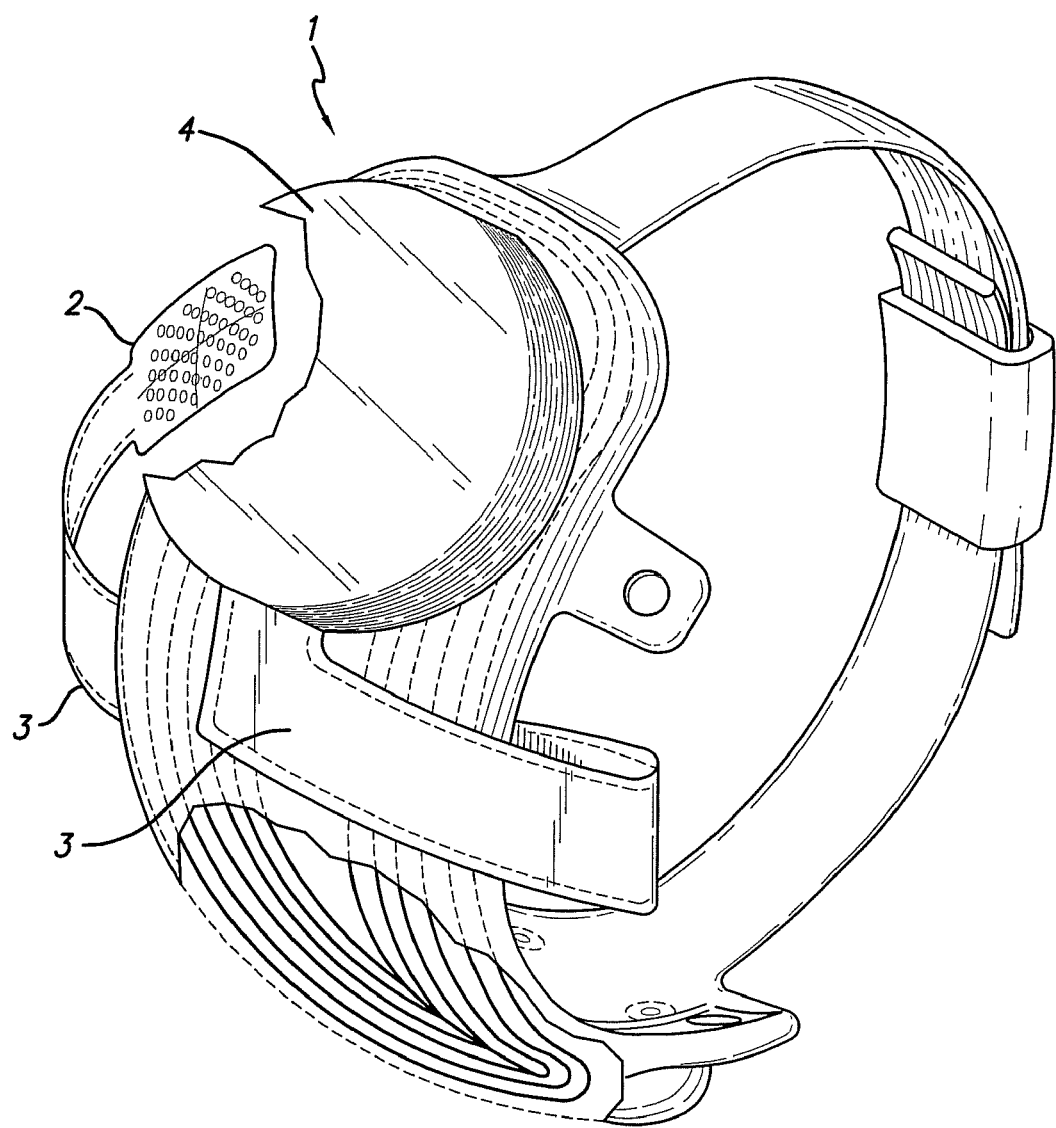
FIGS. 1 and 2 show a retinal stimulation system.
Figure 2:
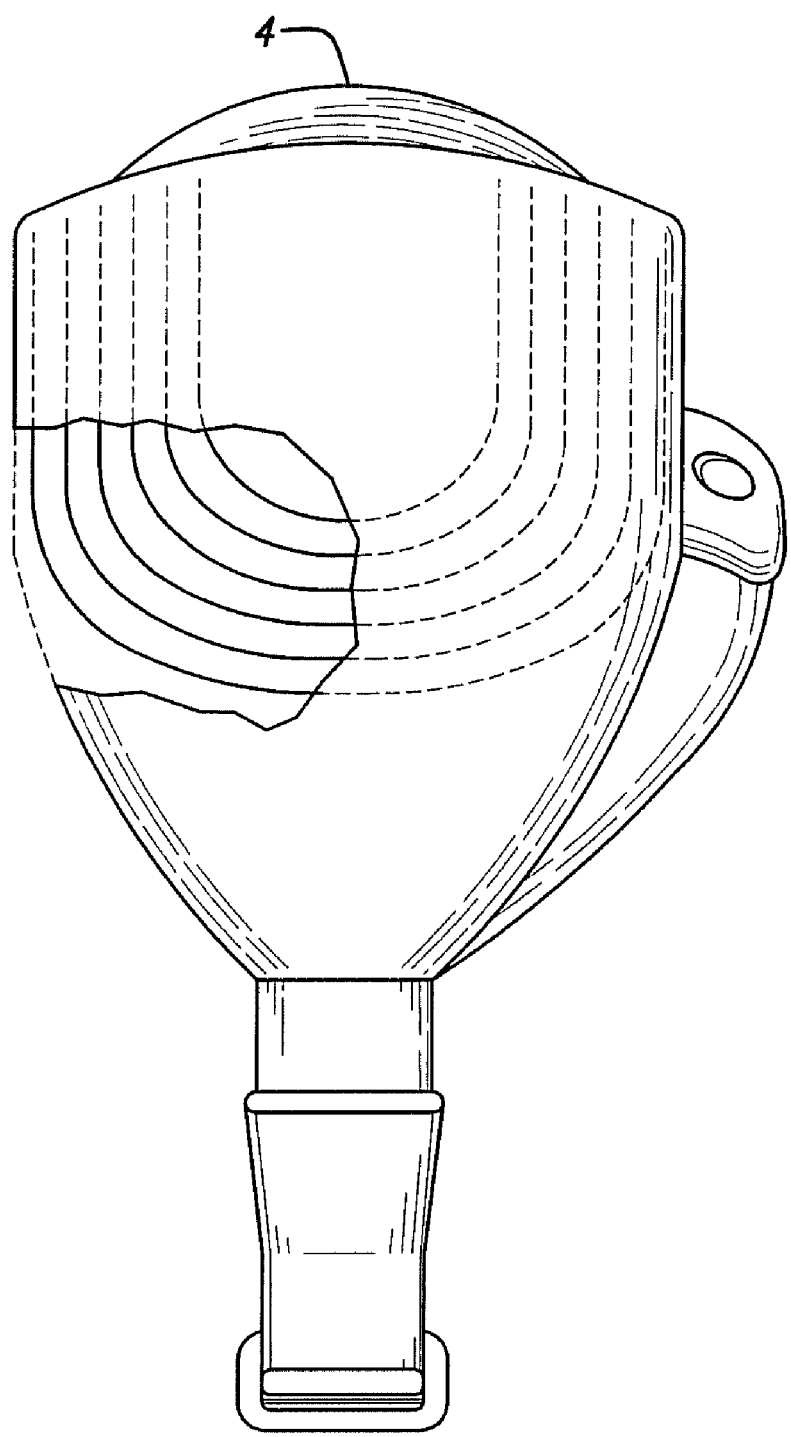

A Retinal Stimulation System, disclosed in U.S. application Ser. No. 11/207,644, filed Aug. 19, 2005 for "Flexible Circuit Electrode Array" by Robert J. Greenberg, et, al. incorporated herein by reference, is intended for use in subjects with retinitis pigmentosa. FIG. 1 and FIG. 2 show a Retinal Stimulation System 1 wherein a patient/subject is implanted with a visual prosthesis to be fitted, configured and optimized according to the present disclosure.

The Retinal Stimulation System 1 is an implantable electronic device containing electrode array 2 that is electrically coupled by a cable 3 that pierces sclera of the subject's eye and is electrically coupled to an electronics package 4, external to the sclera. The Retinal Stimulation System 1 is designed to elicit visual percepts in blind subjects with retinitis pigmentosa.

The fitting system and method according to the present disclosure may be used to establish the most effective Video Processing Unit (VPU) settings for subjects implanted with a visual prosthesis. The psychophysical testing according to the present disclosure will be used to establish the electrical pulse parameters for stimulating retinal neurons and to determine the optimal method for transforming the video input signal to a useful pattern of electrical stimulation.

Establishing a stimulation level that is just detectable to a subject (threshold) allows establishing the lowest stimulation value to be used when mapping the darkest part of the video image to a stimulation profile. A 150-750 ms train of 10-100 Hz pulses (e.g., nine or ten pulses) may be used as the standard stimulus to determine the threshold. The current threshold for each individual electrode may be determined using a method of adjustment.

Figure 3:
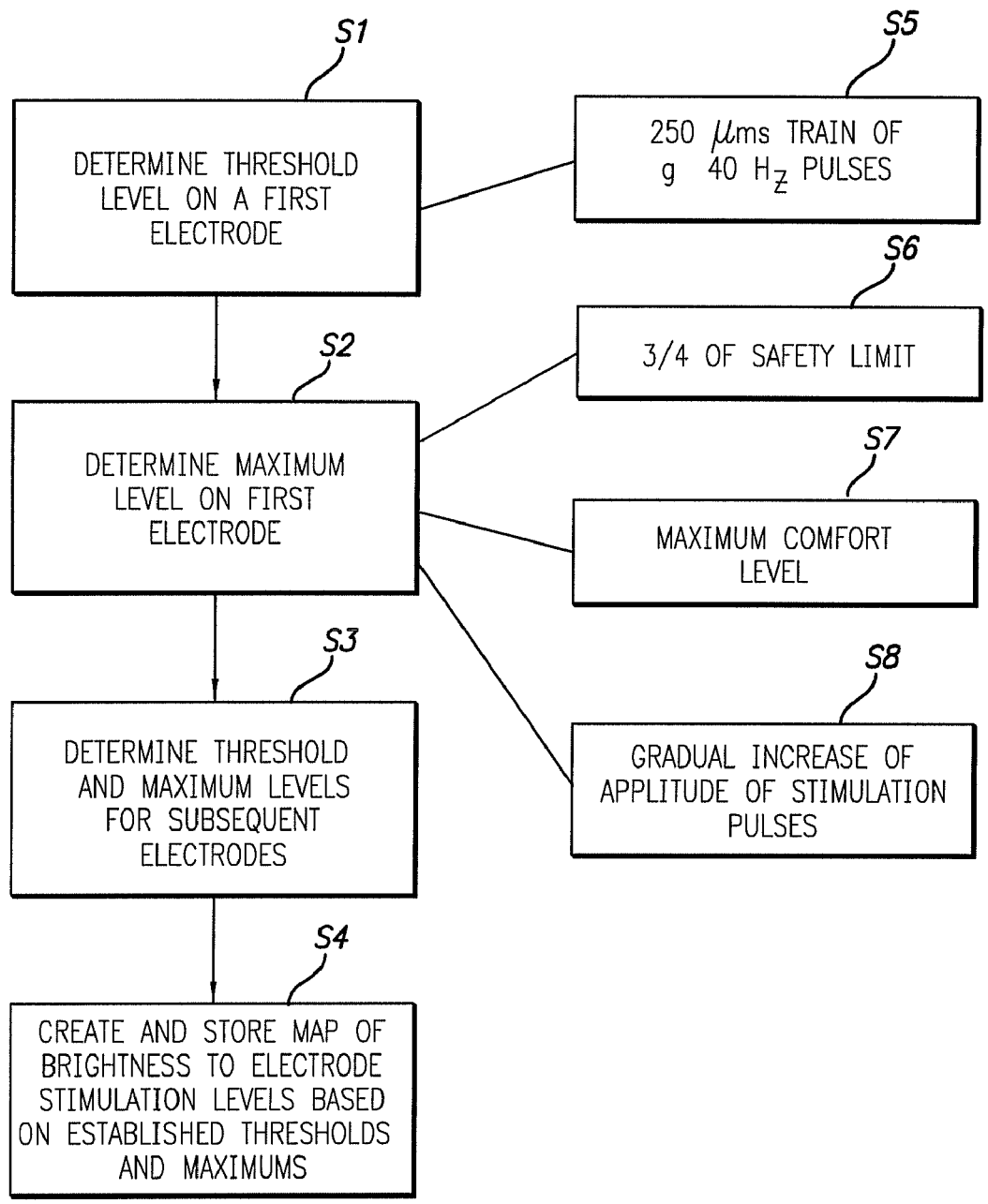
FIGS. 3 and 4 show flow charts listing some of the steps of the visual prosthesis fitting method according to the present disclosure.

Reference can be made to FIG. 3, which shows steps for performing the visual prosthesis fitting method according one of the embodiments of the present disclosure. The threshold level of a first electrode is initially determined in S1. The maximum level of the first electrode is then determined in S2.

Threshold and maximum levels for subsequent electrodes are determined in S3. A map of brightness to electrode stimulation levels based on the established thresholds and maximums is created and stored in S4. As shown in S5, the threshold level of the first electrode can be determined through a 250 ms train of nine 40 Hz pulses. As shown in S6 and S7, the maximum level on the first electrode can be determined by either reaching 75% of the chare density safety limit or by reaching the maximum comfort level of the subject. Finally, S8 shows that the maximum level can be reached by gradually increasing the amplitude of the stimulation pulses.

Figure 4:
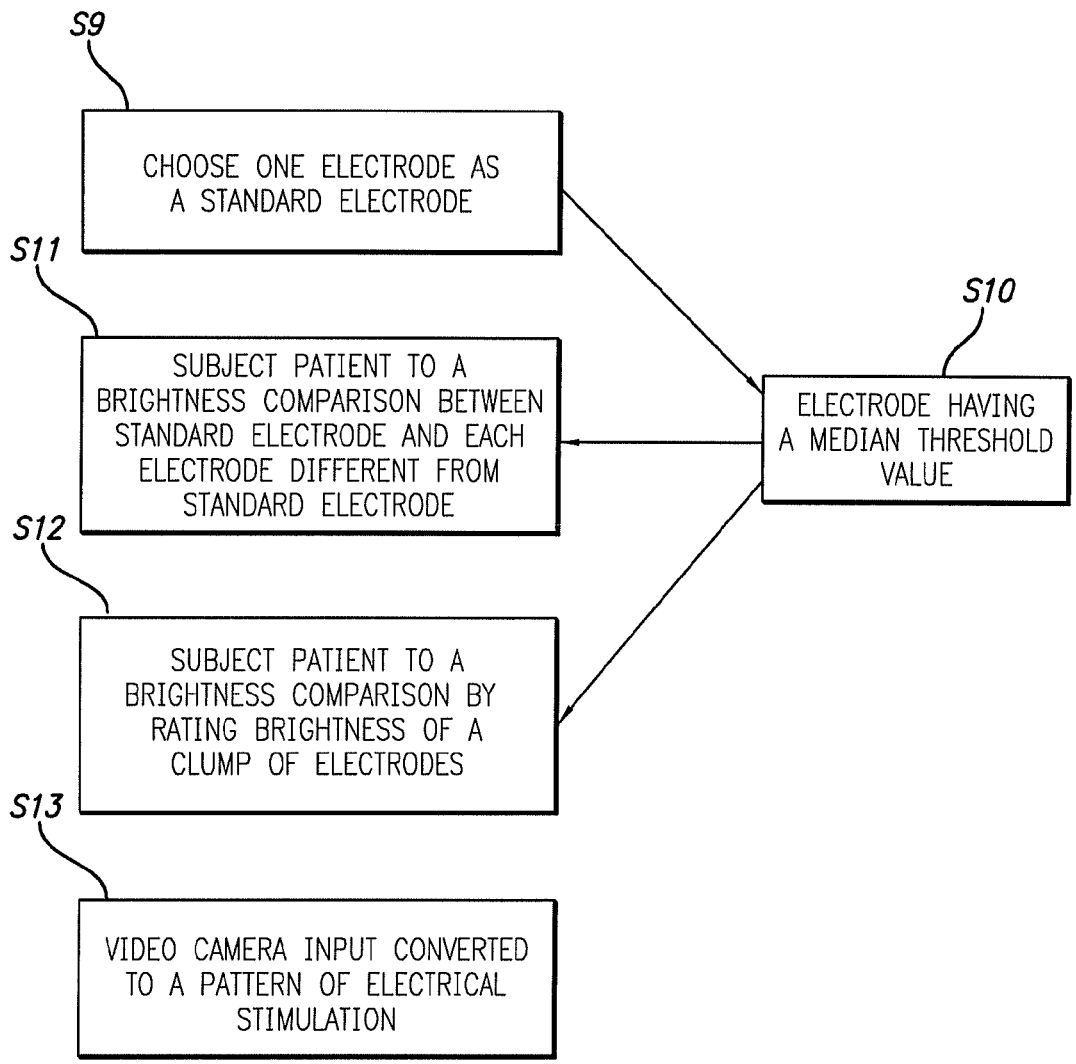

Electrode brightness rating measurements will allow to equate the stimulation levels of different electrodes so that they produce phosphenes of equal brightness. This is because different electrodes have different gains, i.e. the relationship between stimulation level and perceived brightness varies from electrode to electrode. A 250 ms train of 40 Hz pulses (a train of 9 pulses) may also be used as the standard stimulus for rating the brightness of each electrode. As also shown in step S9 of FIG. 4, one electrode (e.g., the electrode from the 32 electrodes in the center of the array that has the median threshold value, see S10 in FIG. 4) may be chosen as the "standard" electrode. As already seen from S6 and S8 in FIG. 3, amplitude of the pulses may be gradually increased by the experimenter until the standard electrode is at 75% of the safety limit for chronic use. This stepping up is to prevent pain sensation when stimulating the standard electrode.

If the maximum comfort level is reached before the safety limit then the experimenter should: (i) Choose a different electrode to be the standard electrode. In this case, the more sensitive electrode that was the initial standard electrode becomes a test electrode. (ii) If the second choice of standard electrode also results in pain when stimulated below the safety limit then set a "maximum" limit based on subject's comfort rather than safety limits. In this case the comfort limit is treated exactly as the safety limit for the process of brightness matching.

Once the amplitude of the standard stimulus has been chosen, the brightness due to that stimulus will be defined as a "10." Each of the electrodes will be stimulated at its maximum chronic level and the subject will rate the relative brightness, for example, 20 if it is twice as bright as the standard, 5 if it is half as bright. The subject will compare the brightness of every electrode with reference to the standard electrode. Two pulses will be presented, and the subject will say which stimulus interval seemed brighter. See S11 in FIG. 4. This may be performed until brightness matched map across all electrodes with reference to the standard electrode.

The procedure for converting a video camera input to a pattern of electrical stimulation can be broken down into two general parts: the video chain and the electrode map (emap).

The Video Chain

The image is initially captured by a video camera mounted on the frame of the glasses. This video image is sent to a Video Processing Unit (VPU), where the video input signal (e.g., NTSC video input signal) is converted to a digital image. This digital image is processed by a series of digital filters. The goal of these operations is to construct a processed video image that is to be presented to the retina by way of electrical stimulation. This includes any contrast, brightness or zoom manipulation as well as any additional filtering to convert the video image to the inferred "neural image" best suited for presentation to the retinal circuitry.

The goal of the video chain is to output an image that is to be presented to the retina. This image to be presented to the retina should have sufficient spatial resolution and a large enough field of view to accommodate any spatial transformation needed to construct the emap (see below). The image to be presented to the retina should consist of intensity values that are scaled from black (0) to white (255) in a way that allows it to maximize the dynamic range for perceived brightness generated by the emap (see below).

The Electrode Map (emap)

The emap specifies the method for converting the output of the video chain to the temporal pattern of stimulation values for each electrode and involves Spatial Mapping and Brightness Mapping.

The output of the video chain is an image that has higher resolution than the electrode array. The goal of the Spatial Mapping is to determine which parts of the image are mapped to the individual electrodes. The video image may be initially mapped to the electrodes using the retinotopic co-ordinates (measured using fundus photograph) of the electrodes. A matrix transformation procedure may be used to sub-sample the image down to the resolution of the electrode array. These procedures will not be described here in detail because known per se to the person skilled in the art.

The above described basic retinotopic organization may be checked using two-point discrimination. In particular, pairs of electrodes may be presented in close temporal sequence and subjects may be asked about the relative position of the pair, e.g. did the dot pair move Left-Right or Right-Left. For example, subjects should be performing Up-Down discriminations for electrodes that are aligned horizontally in retinotopic co-ordinates.

Another method for determining the spatial mapping is to determine the map of the locations of the phosphenes generated by every electrode in the array and use this map to determine which sections of the image each electrode is mapped to. The phosphene locations can be obtained by stimulating an electrode and asking the subject to place a reflective ball in the 3D location of the phosphene. The 3D location of the ball can be measured with an infrared stereo camera system. The advantage of this technique is that it directly takes into account any spatial distortions in the perceived locations of the electrodes or phosphenes. The disadvantage is that it requires the experimenter to obtain a map of the phosphenes generated by every electrode. Interpolation techniques may be used to determine the spatial map of the phosphene locations without making a measurement for every electrode. If the mapping is orderly, it may be possible to sample fewer electrodes and still be able to map the distortions in the perceived locations of the electrodes or phosphenes.

Once it has been determined which parts of the image are mapped to which electrode, a single number will be determined to represent the brightness of that section of pixels in the image through Brightness Mapping. Various methods could be used to determine this value. For instance, the maximum value, the median value, the mean value, the mode, or the minimum may be used. This selection determines the single intensity value that is to be transmitted to the retina, through an electrical stimulation protocol.

Figure 45:
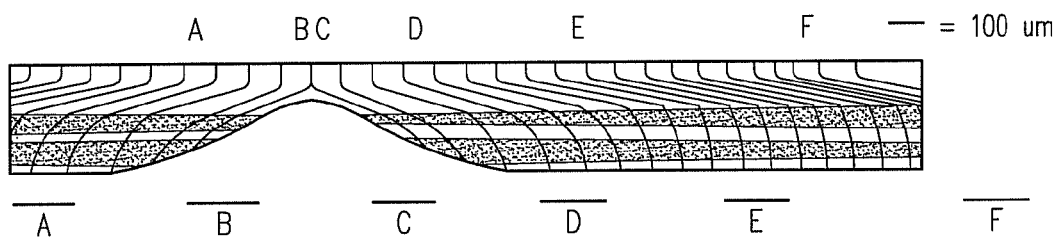
FIG. 45 shows a side view of the human fovea.

The method of fitting Retinal Stimulation System 1 according to the present disclosure may include a technique for mapping the position in the visual field of the phosphenes produced by stimulating each electrode in the electrode array 2 of FIG. 1. These phosphene locations may then be overlayed on the video image to determine the spatial regions of the video image that are mapped to each electrode. For example, in FIG. 45 one would expect that the regions of the human fovea in the center part of the video image that are mapped to electrodes B and C to be smaller than the regions of the video image mapped to electrodes E and F.

Figure 46:
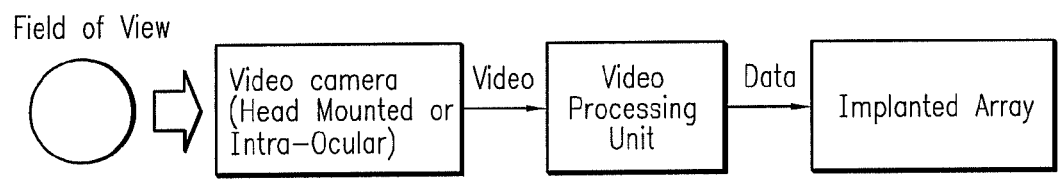
FIG. 46 shows a block diagram of a visual prosthesis.

A block diagram of a visual prosthesis in the Retinal Stimulation System 1 is shown in FIG. 46. The procedure for converting video camera input to a pattern of electrical stimulation can be broken down into two general parts: 1) the video chain and 2) the electrode map (EMAP) as described above in paragraphs [0038]-[0040].

Figure 47:
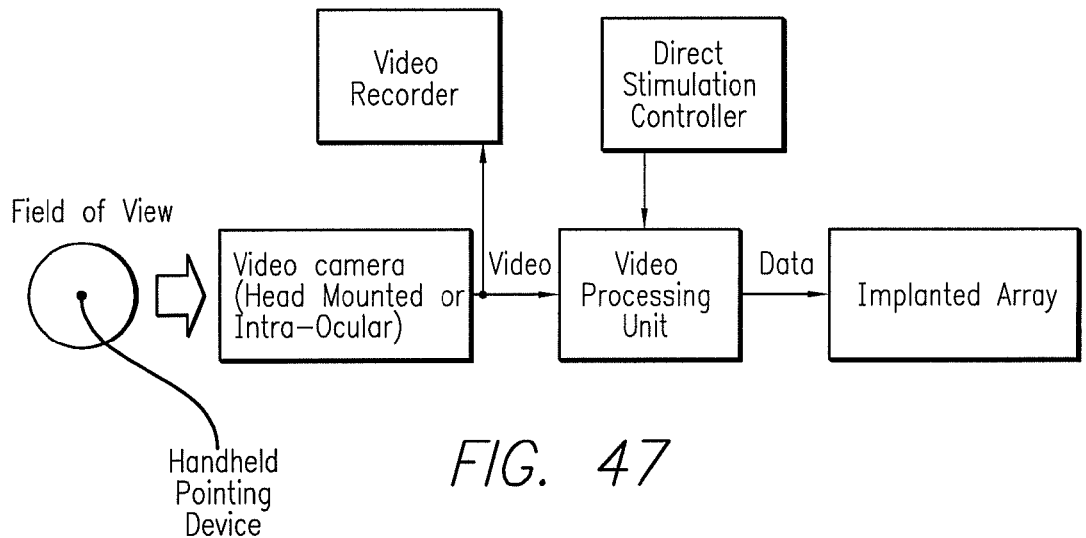
FIG. 47 shows a system for direct stimulation of electrodes and recording the spatial location of resulting phosphenes.

The electrodes in the electrode array 2 of FIG. 1 of the visual prosthesis can be stimulated individually under computer control as shown in FIG. 47. This direct method of stimulating the electrodes is distinct from video mode, where the video image determines the spatio-temporal pattern of electrode stimulation.

Each electrode in the electrode array 2 of FIG. 1 produces a phosphene when stimulated. Each electrode may be stimulated with the Direct Stimulation Controller and the subjects will be instructed to trace the outline of the phosphene on a board placed in front of them using a handheld marker. A video splitter may be used to tap into the output of the video camera and the subject's indication of the phosphene location is recorded with a Video Recorder. An automated image tracking program may be used to find the coordinates of the marker, which gives a measure to the position of the phosphene in the video image.

The method according to the present disclosure provides a direct measurement of the individual phosphene locations within the video image. Because the video image that is recorded is the same video signal that serves as the input to the prosthesis during normal stand-alone system use, this allows a direct mapping between each electrode and the section of the video image that should be map to this electrode.

Figure 48:
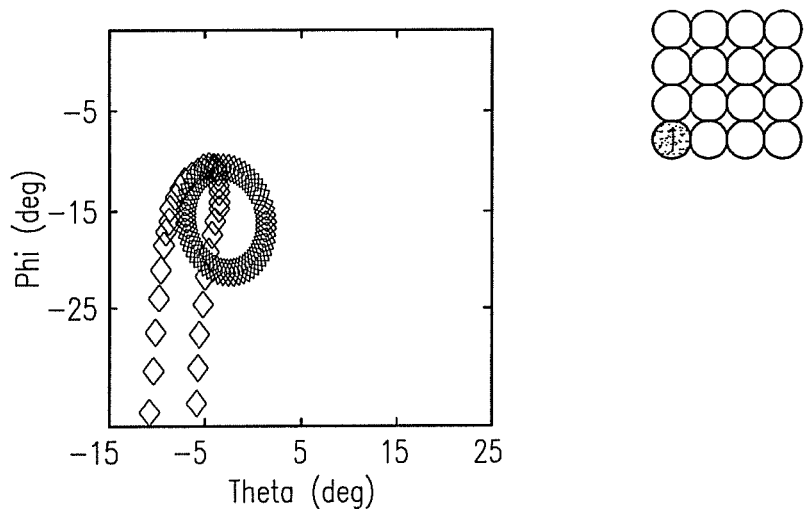
FIG. 48 shows a single electrode phosphene map.
Figure 49:
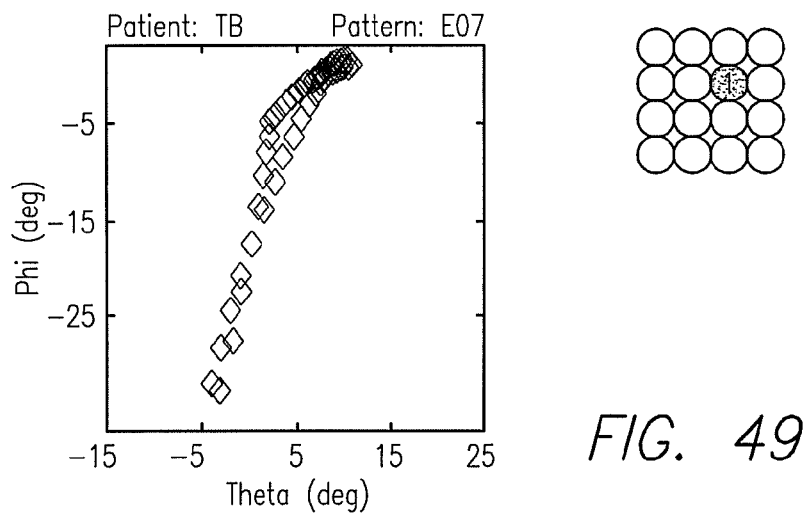
FIG. 49 shows a single electrode phosphene location map.
Figure 50:
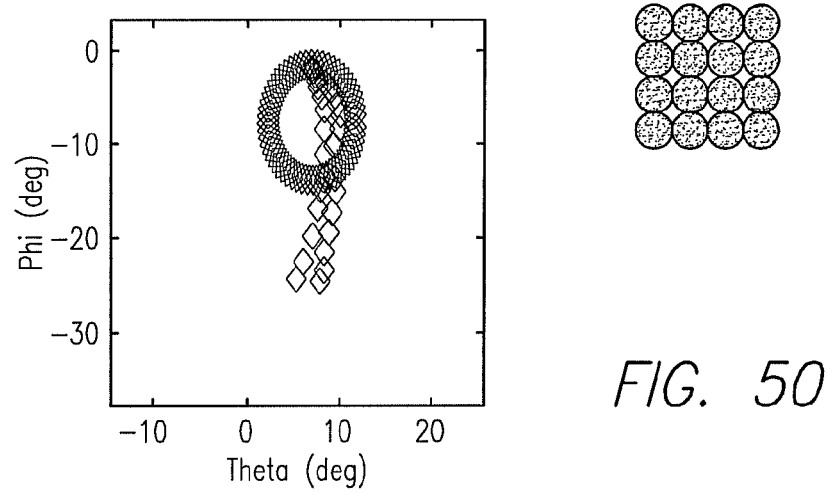
FIG. 50 shows an entire array phosphene location map.
Figure 51:
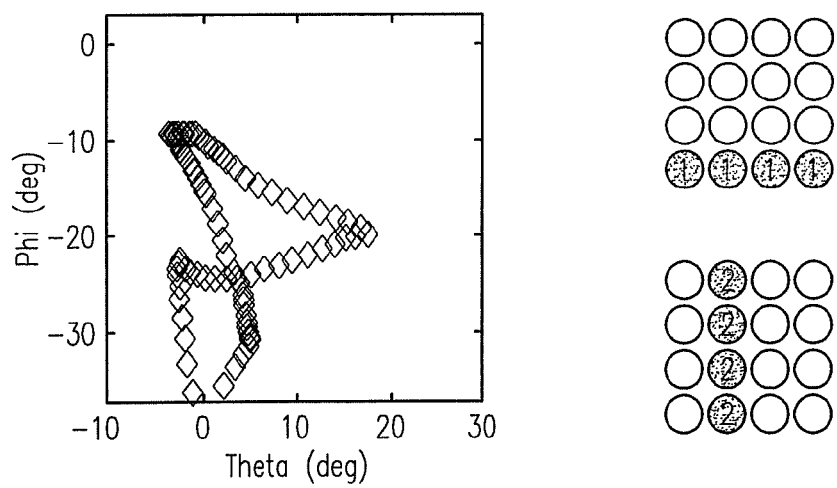
FIG. 51 shows phosphene resulting from simulation of a row and column.

FIGS. 48 and 49 show graphs of the phosphene locations recorded by the camera and processed by the automated image processing program for stimulation of two different individual electrodes in a 16 electrode epiretinal prosthesis. FIG. 50 shows the traced outline of the phosphene resulting from stimulation of all of the electrodes in the array. FIG. 51 shows the perceived phosphene traced by the subject when a row and column are stimulated together.

The results of these mappings may then be used to construct a lookup table that specifies which sections of the video image are used to determine the stimulation level sent to a given electrode. For instance, if a phosphene produces a large circle in the upper-left part of the video image, then the stimulation sent to this electrode is determined by analyzing that part of the video image in real-time.

This method of mapping the video image to the spatial pattern of stimulation accurately corrects any spatial distortions of the retinotopic map. It can rapidly and easily be done and results in a spatial map that is customized for each individual subject.

The goal of the Brightness Mapping procedure is to produce a perceptual brightness level that corresponds to this intensity value. This can be accomplished in a number of different ways. For instance, by varying the pulse amplitude to control brightness (amplitude coding), the pulse frequency (frequency coding), the pulse width, or directly modulating the ganglion cell output with short electrical pulses of varying frequency (temporal coding). The emap needs to ensure that equally bright image values are transformed into stimulation patterns that give as a result equally bright phosphenes. This mapping is established by determining the pulse parameter value to be mapped to the minimum image value (0) for each electrode, determining the pulse parameter value to be mapped for the maximum image value (255), and determining the mapping for the intermediate values.

For amplitude coding, the 0 intensity value may be set to be equal to the threshold pulse amplitude for every electrode. For the electrode with the median threshold, the 255 intensity value may be set to the maximum safe current level. The more sensitive electrodes will have the 255 intensity value mapped to the current amplitude that matches the brightness of the median electrode at its maximum current level. When the less sensitive electrodes are set to their maximum amplitude, they will be perceptually dimmer than the median electrode at its maximum amplitude. Every electrode will linearly map the intensity values to the amplitude range between the specified min and max values. For the less sensitive electrodes, the maximum intensity value that can be brightness mapped to the median electrode, and all higher intensity values, will be mapped to the maximum amplitude.

Electrode interactions can be calculated by stimulating "clumps" of multiple electrodes (e.g., 2×2 or 4×4).

Figure 5:
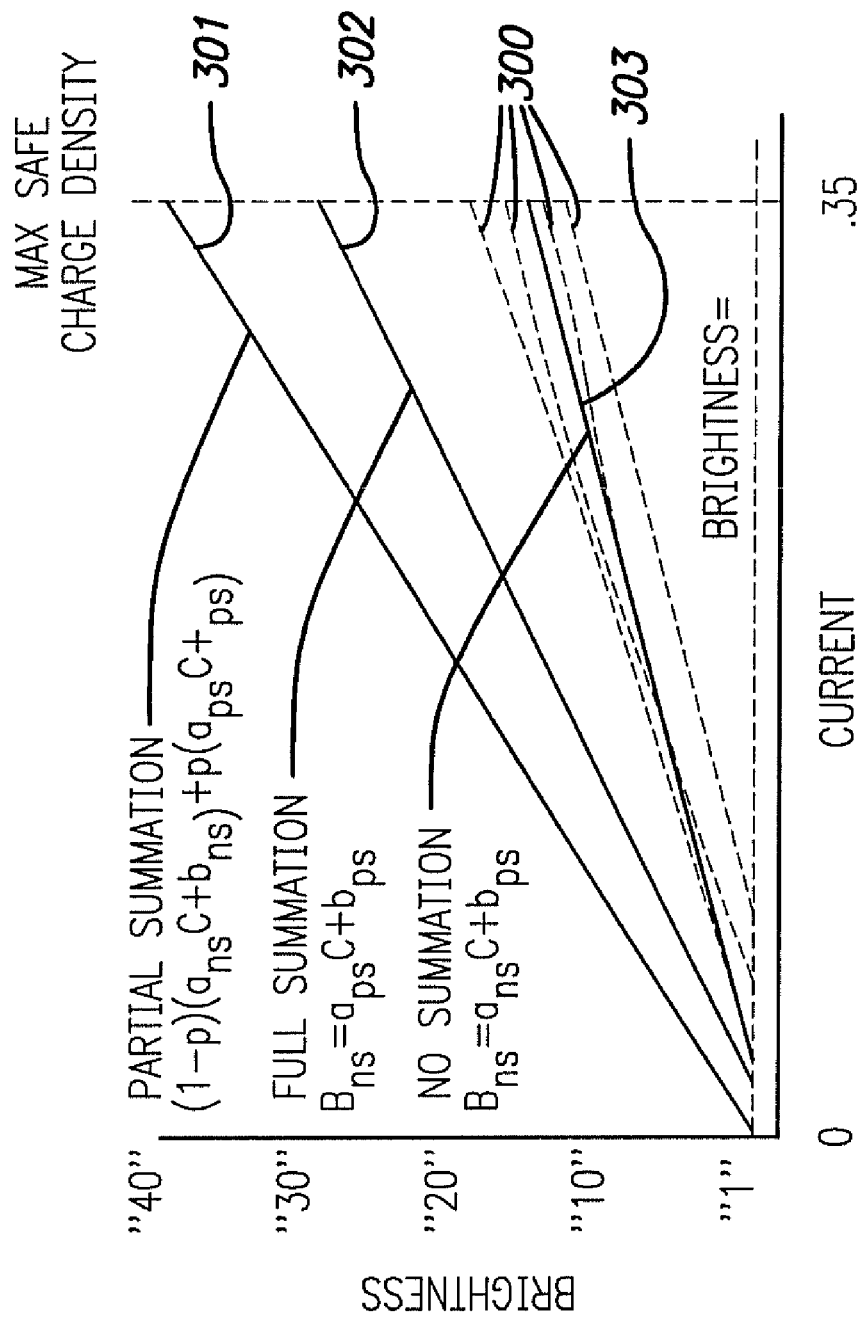
FIG. 5 shows a current v. brightness diagram of brightness functions.

In FIG. 5, the brightness functions for individual electrodes are shown by dotted lines 300. The threshold may be considered as having a brightness of "1". The subjects may be asked to rate the brightness for the clump at maximum safety levels (again in comparison to the "standard" single electrode at the center of the array). See also S12 in FIG. 4. If the brightness doesn't sum across the electrodes, then the threshold current level should be the minimum threshold current of the four electrodes (the threshold for the most sensitive electrode) and the brightness rating for the clump on max should be the mean brightness rating of the clump of electrodes, as shown by the line 303 in FIG. 5. If the brightness sums across electrodes fully then the threshold current would be the sum of the currents (~¼ the individual currents for a 2×2 clump) and the apparent brightness of the entire clump of electrodes would be the sum of the clump (~4× the brightness of the individual electrodes for a 2×2 clump), as shown by line 301 of FIG. 5.

It is likely that summation will be somewhere between the two extremes 301 and 303, as shown by line 302 of FIG. 5. The summation can be calculated as brightness rating of clump=$(1-p)(aBnsBC+bBnsB)+p(aBpsBC+BpsB)$ where $BBnsB=aBnsBC+bBnsB$ is the predicted brightness rating equation for no summation, and $BBpsB=aBpsBC+bBpsB$ is the predicted brightness rating equation for perfect summation. p is the amount of summation across electrodes—when p=1 there is perfect summation, p=0 means there is no summation. If p is significantly larger than 1 then the lookup tables may be based on the assumption that a certain number of electrodes will be stimulated at a given time.

The subjects may be asked to rate the brightness of current amplitudes halfway between threshold and max brightness level. If the linear model is correct, the brightness rating value should be roughly midway between the rating of the max brightness level and 1. If not, fit the data with a suitable nonlinear function such as a power function.

A check for spatial homogeneity may also be performed. In other words, it is checked whether neighboring electrodes do have similar brightness functions for both threshold values, and for the brightness rating at maximum safe charge density levels.

Figure 6:
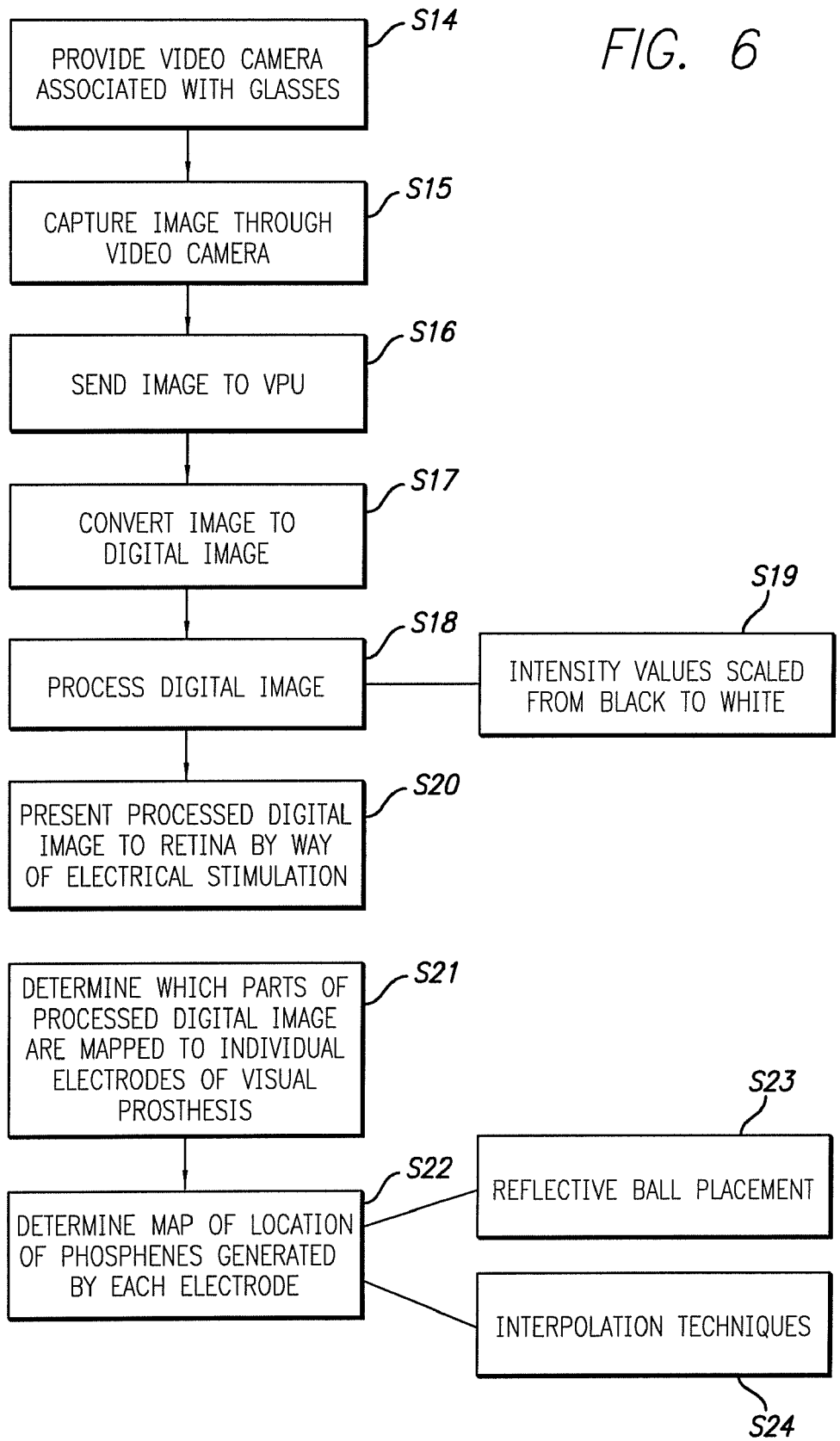
FIG. 6 shows a flow chart listing some of the steps of the visual prosthesis fitting method according to the present disclosure.

A summary of the procedure described above is shown in FIG. 6. A subject is provided with a video camera associated with a pair of glasses (S14). An image is captured through the video camera (S15). The image is sent to a video processing unit VPU (S16) and converted to a digital image (S17). The digital image is processed (S18), its intensity values being scaled from black to white (S19), and presented to the retina of the subject or patient by way of electrical stimulation (S20). The above procedure also determines which parts of the processed digital image are mapped to individual electrodes of the visual prosthesis (S21) and determines a map of location of phosphenes generated by each electrode (S22). This can be done either by a reflective ball placement (S23) or by means of interpolation techniques (S24).

Testing Methods to Confirm Fitting

In a typical eye exam, a simple stimulus (a letter) may be used and an optometrist tries two lenses and asks us which one looks better. The optometrist uses this to gradually iterate to an optical prescription. This can be used to quickly determine whether a change in stimulus parameters (e.g. frequency) might possibly suit a patient better. It will also help to determine whether any changes in stimulation protocol or engineering design over time is really resulting in improved performance in patients. One possible fitting image might be of about 16 electrodes simultaneously stimulated.

Spatial Resolution Test

Subjects have to decide whether the resulting rectangle is horizontally or vertically oriented. The task can vary in spatial difficulty as follows (from easy to hard); 8×2, 7×2, 7×3, 6×3, 5×3, 5×4.

Brightness Linearity Test

Brightness maps may be examined by varying the brightness of the square compared to the background and either asking subjects to rate the evenness of the square in terms of its brightness (implying that the brightness across electrodes is well matched) or rate the brightness of the square (to measure whether the clumped estimated brightness maps are suitably linearized).

After the implantation of the visual prosthesis in the subject, the following examinations may be done on the subject with the device ON and OFF to provide control measures that can be used to optimize the device.

Electrode Impedance may be used to determine the electrical characteristics of the array interface with the retina. Using the "Measure Impedance" of the Fitting System described below, electrode impedances will be recorded on all electrodes via the VPU.

Electrode Threshold may be used to determine the minimum stimulation required to elicit a percept from one electrode. The stimulation may be performed using single pulses, cathodic first, with all waveform phases set to 0.45 ms using the Fitting and Psychophysical Test Systems disclosed below. The subject may control the amplitude of the test pulse and will manipulate it up and down until he/she has determined the level at which a phosphene is just detected.

A First Stimulation Procedure may be used to expose the subject to electrical stimulation using the Fitting System described below and record the subject's initial observations and responses. The following may be done to perform the test.
a. The external Fitting system may be configured for Communications Mode. A separate Operating Room coil may be used if there is residual swelling at the implant site which would make wearing the Camera/Glasses uncomfortable or painful.
b. An electrode impedance will be obtained.
c. A single electrode will be selected for initial stimulation.
d. The amplitude of stimulation will be increased and the subject asked to describe any sensation. If a percept occurs, the subject will be asked to describe it.
e. Testing may be repeated on subsequent electrodes.
f. At the discretion of the investigator, multiple electrodes may be stimulated simultaneously using the procedure above.

A VisQOL (vision and quality of life) survey can be used to evaluate the vision related quality of life of the study subjects. The VisQOL Health Survey is a health-related quality of life instrument that has been validated and used in low vision subjects. The use of this instrument may provide a baseline for the general quality of life for the subjects and the impact of a retinal implant on their outlook. This instrument will be given to the subject pre-implant, then at prescribed intervals post-operatively. Each question of the VisQOL survey may be read aloud to the subject and the response recorded. Results will be scored according to the published methods for the survey.

A Massof Inventory may be used to evaluate the vision related activities of daily living of the study subjects. The Massof Inventory is a series of activity related questionnaires that allow discrimination of both the usefulness and the difficulty of each task. Through the evaluation of tasks the subject finds useful or pleasurable, the inventory provides a measure of the "real-world" daily living changes, rather than artificial constructs. This yields a meaningful measure without the risks of the subject "training to the test." Each question of the Massof Inventory may be read aloud to the subject and the response recorded. Results will be scored according to the published methods for the survey.

A Functional Assessment of Self Reliance on Tasks (FAST) may also be used to evaluate the vision related activities of daily living of the study subjects. The FAST instrument has been developed by the Southern Arizona VA Health Care System, Blind Rehabilitation Service for the evaluation of the progress of subjects with degenerating vision during rehabilitation. In the instrument, clinical observers rate the subject's ability to perform simple daily living functions on a 1 to 10 scale. Each item of the FAST is evaluated by site staff trained in the instrument. Each item on the instrument will be evaluated serially. Results will be scored according to the published methods for the instrument.

A Psychophysical Test may be used to provide potential subjects with an experience similar to post-operative psychophysical testing. Due to the intensive nature of the post-operative psychophysical testing, subjects may be tested using an auditory test. This test will not be used to evaluate hearing. Each potential subject may be provided headphones connected to a tone generator. A single tone of 0.5 seconds will be presented. A second tone of a different loudness (with the same frequency) will then be presented. The subject will be asked which tone they perceived as louder. The test may be repeated twenty times.

Spatial Mapping of Phosphenes can be used to determine the relationship between the physical positions of the individual electrodes on the retina and the perceived locations of the phosphenes induced in the subject's visual field. Before every trial, the seated subject will be instructed to place a magnetic token on a wall-mounted metal board in the position felt to be "front and center". This position will be taken to be coordinate position (0, 0). A randomly chosen electrode may then be stimulated with a single 0.45 ms supra-threshold pulse and the subject instructed to position a second magnetic token in the perceived location of the phosphene. Each electrode may be stimulated twelve times. The average position of the phosphene corresponding to each electrode, relative to (0, 0), will be calculated. A calibrated, validated three-dimensional tracking system may also be used to capture spatial locations of phosphenes.

Brightness Matching may be used to determine the relationship between electrode stimulation and percept brightness. Brightness matching may be performed using the Fitting and Psychophysics Test Systems described below. The subjects may be presented with a standard current of, for example, 45 µA. The subjects may then be presented with pulses that vary in amplitude and will be asked to indicate which pulse was brighter. This procedure may be repeated multiple times across different electrodes to determine the relative current amplitude. From the data obtained, the current amplitude required to elicit the same perceived brightness for each electrode may be determined.

Motion Discrimination may be used to test the ability of the subjects to correctly discriminate the direction of motion of a high contrast moving bar. The electrode amplitudes are set to 30 µA above the threshold for each electrode. The stimulation will be set to a temporal frequency that was comfortable for each subject. For the experiments done with the camera, the camera zoom will be set to provide a 1:1 matching of the visual angle subtended by the array on the retina. The experimental paradigm is a four alternative forced choice paradigm (4AltFC). For the first experiment, the electrodes on the array may be directly stimulated by a bar (horizontal or vertical in shape; 10°×2.5°) moving in any one of four cardinal directions (Test Pattern mode). The direction of motion of the bar may be varied randomly on a trial by trial basis. The speed of the moving bar may be varied from approximately 4°/s to 16°/s. The subject will be instructed to identify the direction of motion, and then verbally indicate the direction to the observer. The trials may be repeated in blocks of 20.

For the second experiment, a similar high contrast bar (horizontal or vertical in shape; 10°×2.5°) may be projected onto a screen in front of the head-mounted camera of the subject, moving in any one of four cardinal directions (Camera mode). The direction of motion of the bar may be varied randomly on a trial by trial basis. The speed of the moving bar may be varied from approximately 4°/s to 16°/s. The subject will be instructed to identify the direction of motion, and then verbally indicate the direction to the observer. The trials may be repeated in blocks of 20.

Flicker Fusion may be used to determine the frequency at which repeated stimuli merge. An electrode will be stimulated at different frequencies, with the same pulse parameters. The subject may be asked to report any apparent flickering of the percept.

Orientation and Mobility Task may be used to evaluate the orientation and mobility of subjects. Geruschat, Turano et. al. have used a simple mobility task consisting of a corridor with high contrast obstacles to evaluate the orientation and mobility of low vision subjects. It was found that the time to traverse the course was correlated to visual acuity and field. This study will utilize a greatly simplified course. Each subject will be asked to follow a straight line and in a second test asked to find and touch a high-contrast target on the wall. The subject's time and accuracy will be evaluated. This instrument will be given to the subject pre-implant, then at prescribed intervals post-operatively. Each test may be performed with the implant ON and OFF. The subject may be instructed to walk each predefined course as quickly and safely as possible using any mobility aid. The distance the subject is away from the target at the end of the task and the time to traverse the course will be noted. Each course may be tested three times with the implant OFF and then three times with the implant ON.

Each of the three runs may consist of a different starting position:
  Straight ahead,
  Turned approximately 10° right, and
  Turned approximately 10° left.
The order of the starting positions may be randomly determined by the observer.

Figure 7:
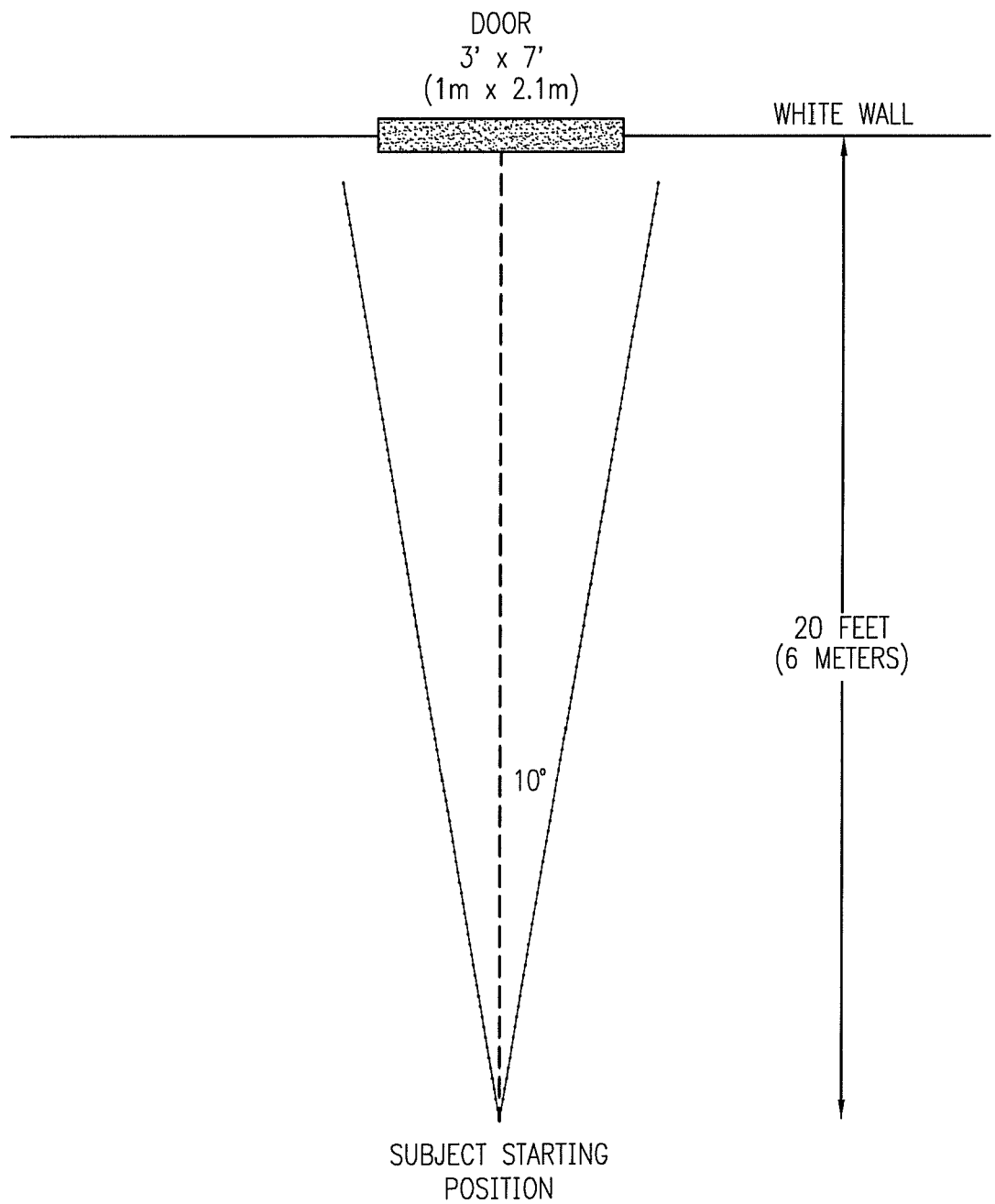
FIGS. 7 and 8 show placements of a subject while performing a vision test.

Referring to FIG. 7, the subject may be placed 20 feet (6 meters) from a wall with a contrasting 3'×7' (1 m×2.1 m) rectangular target "door". The subject will be asked to walk to the "door" and place a hand on the "door". The distance the subject's hand is outside the "door" area (measured perpendicularly) and travel time will be recorded.

Figure 8:
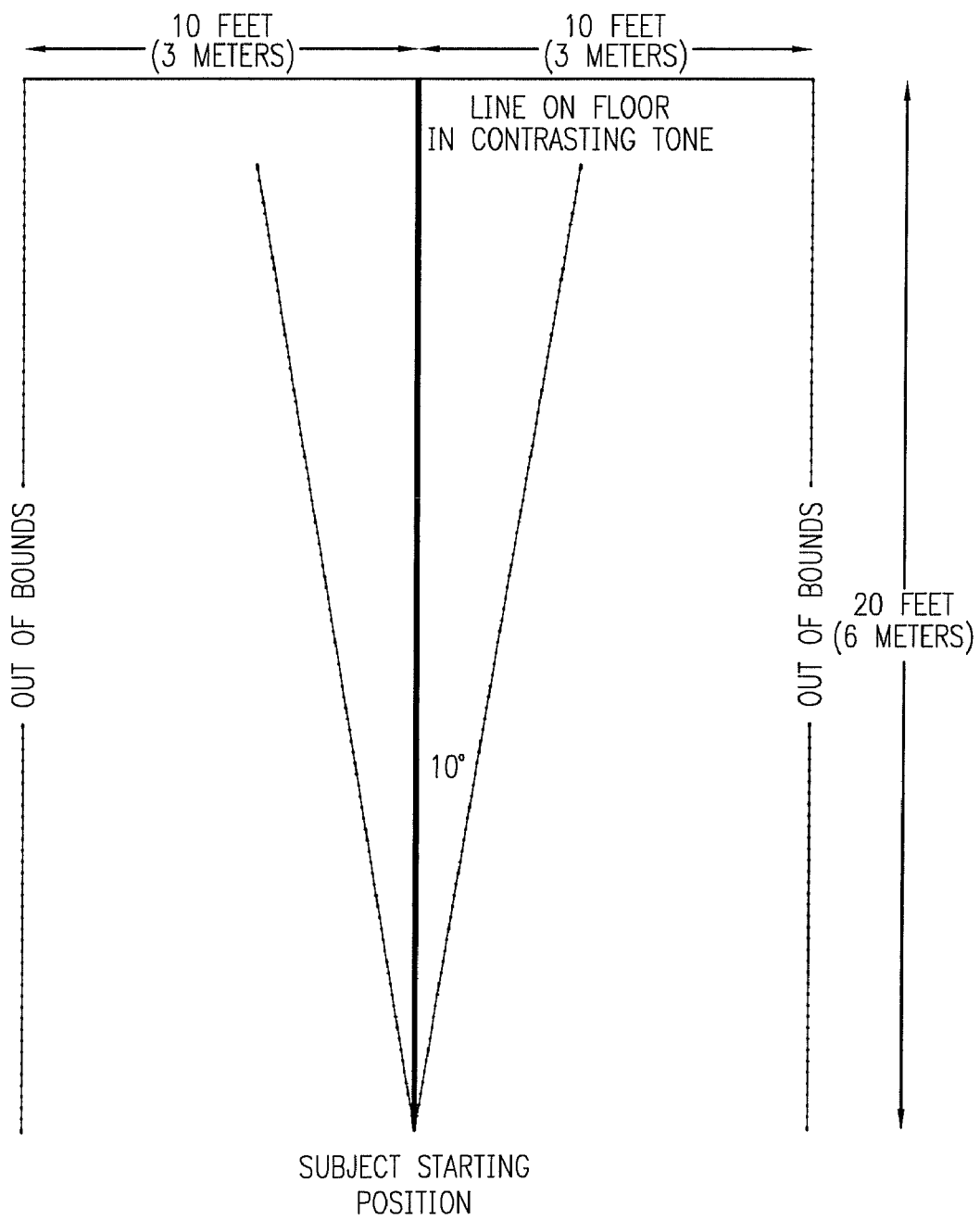

Referring to FIG. 8, the subject may be placed at the start of a line 20 feet (6 meters) long which contrasts with the floor surface brightness. The subject will be asked to walk along the line. At the end of the line, the subject will be instructed to stop. The distance the subject is away from the end of the line (measured perpendicularly from the nearest edge) and travel time will be recorded.

Figure 9:
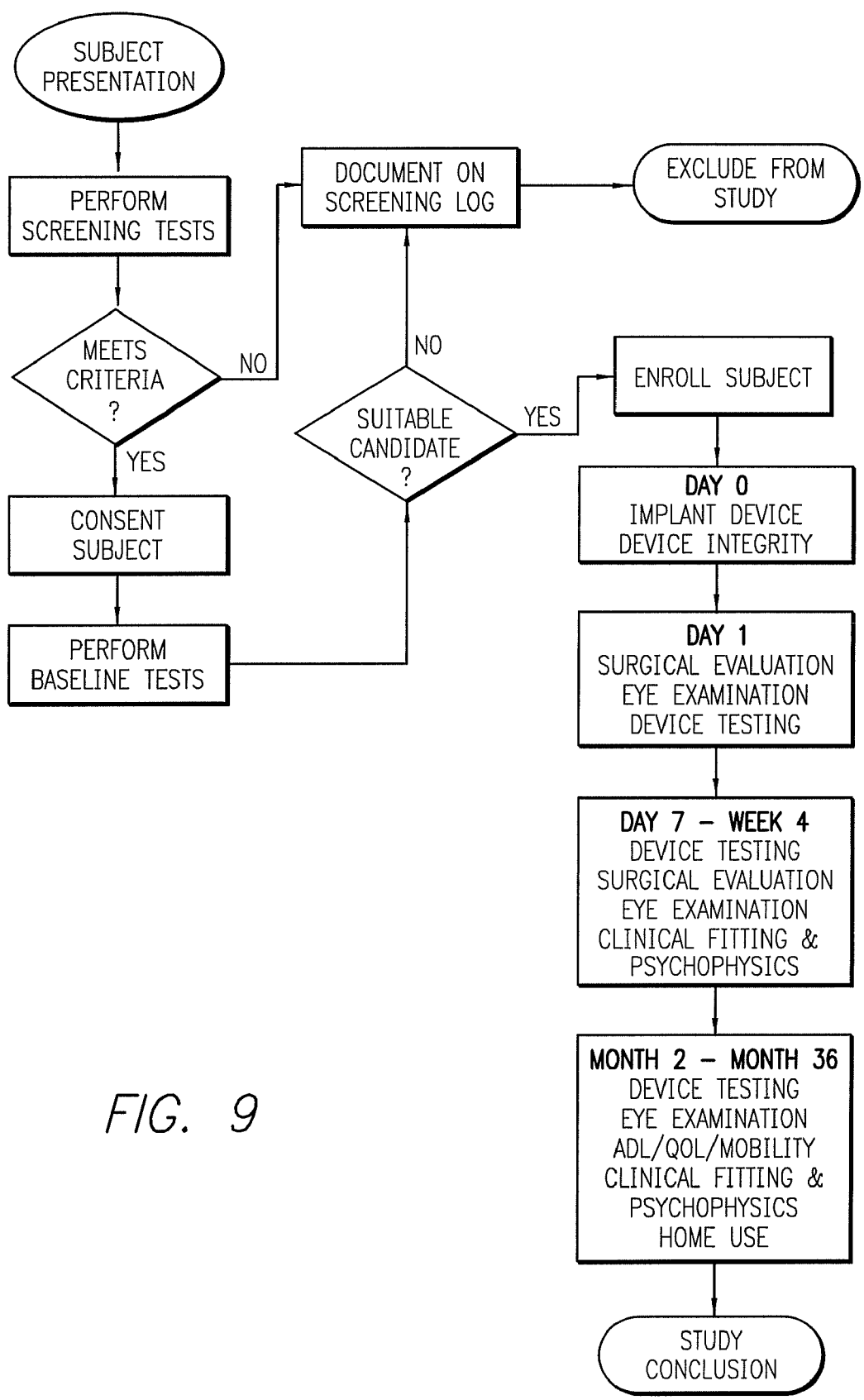
FIG. 9 shows flowchart related to vision tests performed on a subject.

FIG. 9 shows a procedural flow during performance of the methods disclosed herein.

Figure 10:
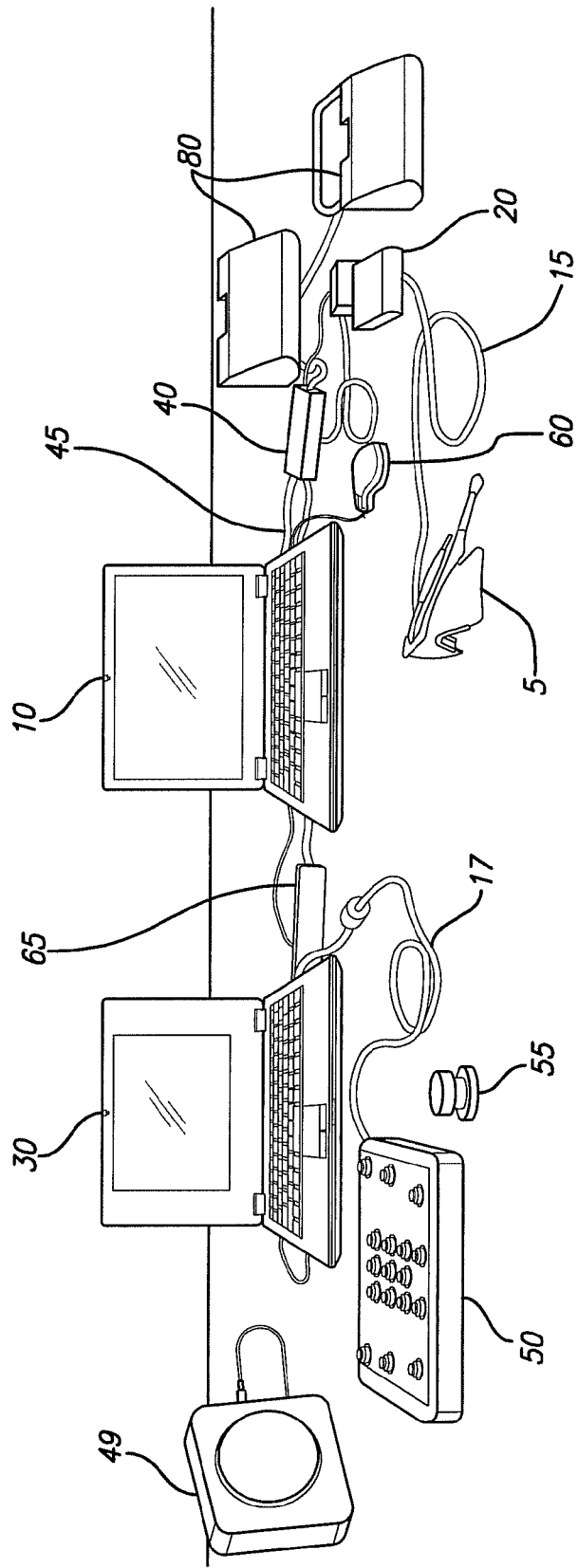
FIG. 10 shows components of a fitting system.

Referring to FIG. 10, a Fitting System (FS) according to the present disclosure may be used to configure and optimize the visual prosthesis 3 of the Retinal Stimulation System 1.

The Fitting System may comprise custom software with a graphical user interface running on a dedicated laptop computer 10. Within the Fitting System are modules for performing diagnostic checks of the implant, loading and executing video configuration files, viewing electrode voltage waveforms, and aiding in conducting psychophysical experiments. A video module can be used to download a video configuration file to a Video Processing Unit (VPU) 20 and store it in non-volatile memory to control various aspects of video configuration, e.g. the spatial relationship between the video input and the electrodes. The software can also load a previously used video configuration file from the VPU 20 for adjustment.

The Fitting System can be connected to the Psychophysical Test System (PTS), located for example on a dedicated laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Any time stimulation is sent to the VPU 20, the stimulation parameters are checked to ensure that maximum charge per phase limits, charge balance, and power limitations are met before the test stimuli are sent to the VPU 20 to make certain that stimulation is safe.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the retinal prosthesis for each subject.

The Fitting System laptop 10 is connected to the VPU 20 using an optically isolated serial connection adapter 40. Because it is optically isolated, the serial connection adapter 40 assures that no electric leakage current can flow from the Fitting System laptop 10.

As shown in FIG. 10, the following components may be used with the Fitting System according to the present disclosure. A Video Processing Unit (VPU) 20 for the subject being tested, a Charged Battery 25 for VPU 20, Glasses 5, a Fitting System (FS) Laptop 10, a Psychophysical Test System (PTS) Laptop 30, a PTS CD (not shown), a Communication Adapter (CA) 40, a USB Drive (Security) (not shown), a USB Drive (Transfer) (not shown), a USB Drive (Video Settings) (not shown), a Patient Input Device (RF Tablet) 50, a further Patient Input Device (Jog Dial) 55, Glasses Cable 15, CA-VPU Cable 70, CFS-CA Cable 45, CFS-PTS Cable 46, Four (4) Port USB Hub 47, Mouse 60, LED Test Array 80, Archival USB Drive 49, an Isolation Transformer (not shown), adapter cables (not shown), and an External Monitor (not shown).

The external components of the Fitting System according to the present disclosure may be configured as follows. The battery 25 is connected with the VPU 20. The PTS Laptop 30 is connected to FS Laptop 10 using the CFS-PTS Cable 46. The PTS Laptop 30 and FS Laptop 10 are plugged into the Isolation Transformer (not shown) using the Adapter Cables (not shown). The Isolation Transformer is plugged into the wall outlet. The four (4) Port USB Hub 47 is connected to the FS laptop 10 at the USB port. The mouse 60 and the two Patient Input Devices 50 and 55 are connected to four (4) Port USB Hubs 47. The FS laptop 10 is connected to the Communication Adapter (CA) 40 using the CFS-CA Cable 45. The CA 40 is connected to the VPU 20 using the CA-VPU Cable 70. The Glasses 5 are connected to the VPU 20 using the Glasses Cable 15.

Figure 11:
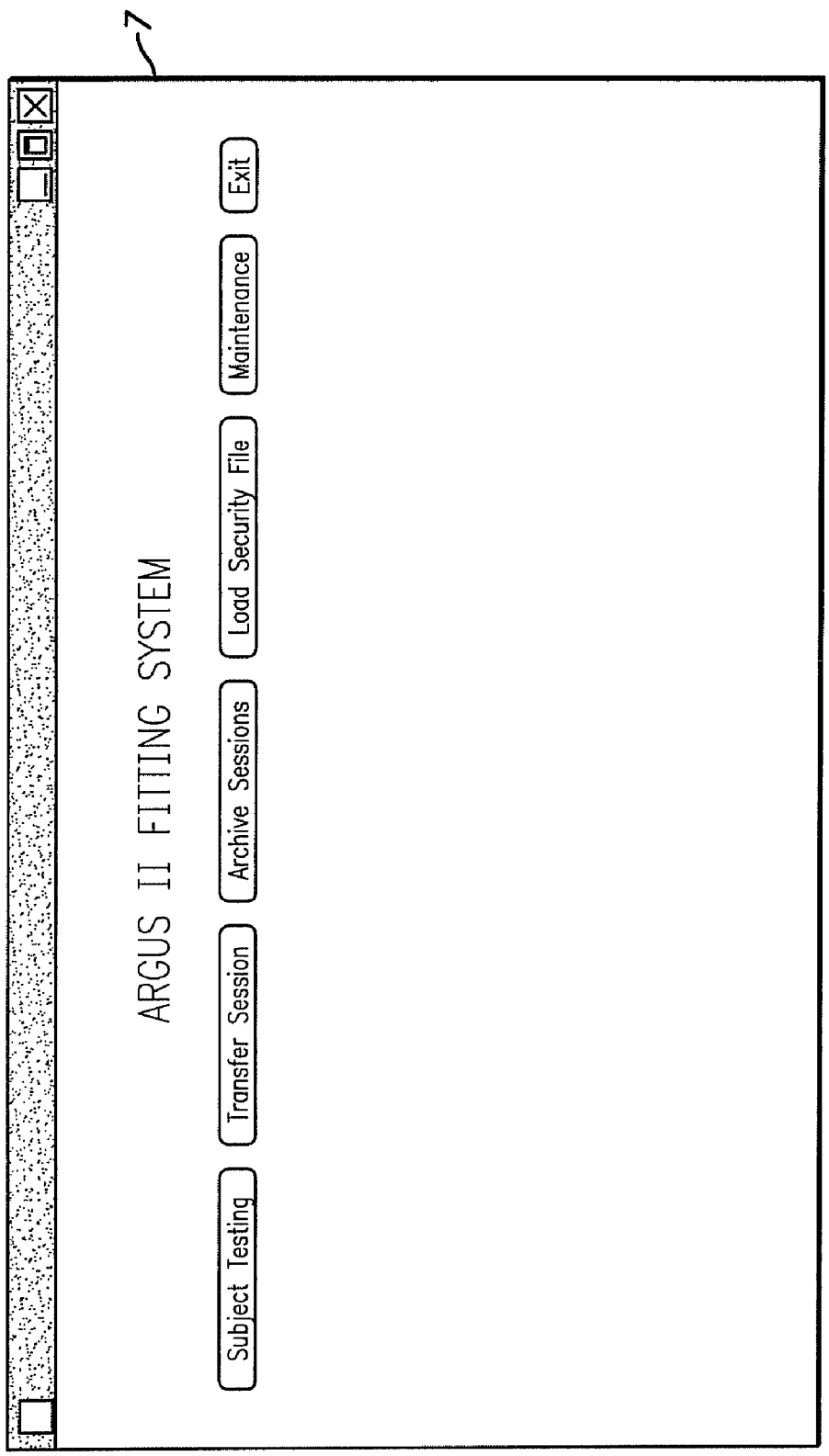
FIG. 11 shows a Main Menu computer screen.

The graphical user interface of the Fitting System may have six options on the FS Main Menu 7 as shown in FIG. 11. For example, Subject Testing, Transfer Session, Archive Sessions, Load Security File, Maintenance, and Exit.

The Subject Testing option may be selected when performing: diagnostic check (i.e. impedance and waveforms) on the status of the implant, viewing waveforms for selected electrodes, loading a video configuration file to the VPU and stimulating the subject using the downloaded video stimulation parameters, executing psychophysical experiments. The Transfer Session option may be selected when copying file(s) to a thumb drive. The Archive Sessions option may be selected when archiving all data files on the FS laptop 10 to the external drive 49. The Load Security File option may be selected to enable use of the Fitting System. The Load Security File option may be chosen at the initial clinical testing session. The Maintenance option may be selected to perform maintenance on one or more components of the system. The Maintenance option may be set up to only be accessed by an authorized person. The Exit option may be selected to close out the main menu.

The Subject Testing option is more fully described in the following paragraphs.

Prior to using a VPU 20 with a new subject for the first time, the following steps may be performed by an authorized person to configure the VPU 20: 1) Confirm that the VPU 20 is configured for use, 2) Match the VPU 20 to an implant, 3) Program the VPU 20 with the Subject's ID, and 4) Label the VPU 20 with the Subject's ID.

Prior using the Subject Testing option, the VPU 20 should be on, the subject should put on the Glasses 5, the Glasses 5 should be adjusted until a link is obtained with the implant, and the VPU 20 should confirm that the implant is working by running start-up tests.

Figure 12:
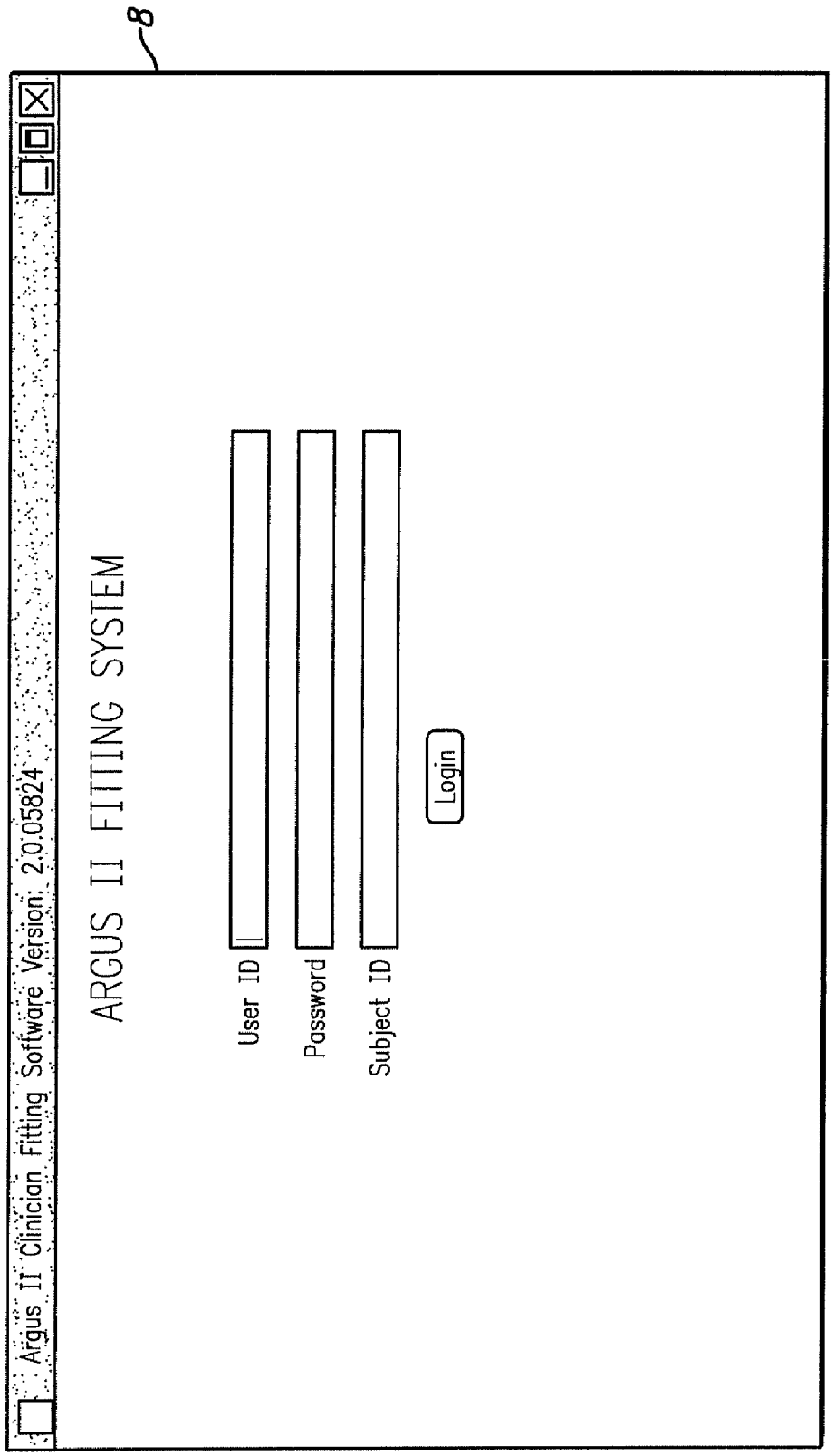
FIG. 12 shows a Login computer screen.

Once the Subject Testing option is selected from window 7, a login screen 8 shown in FIG. 12 may be displayed with fields for User ID, Password and Subject ID.

After the login, a diagnostic application may be initiated to display the status of the implant. Through the diagnostic application, an electrode integrity check may be performed and the electrode status may be displayed and the impedance and waveforms for each of the electrodes can be measured.

Figure 13:
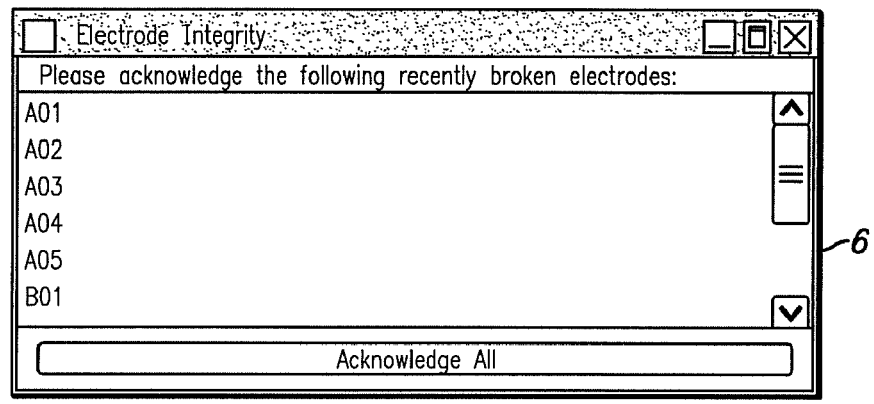
FIG. 13 shows an 'Electrode Integrity' message box.

An "Electrode Integrity" message box 6, shown in FIG. 13, may be displayed in the event that any newly broken/shorted electrodes are detected or broken/shorted electrodes are present. If no newly detected broken/shorted electrodes are detected, this message box will not appear and the diagnostics screen 109 shown in FIG. 14 may be displayed.

Figure 14:
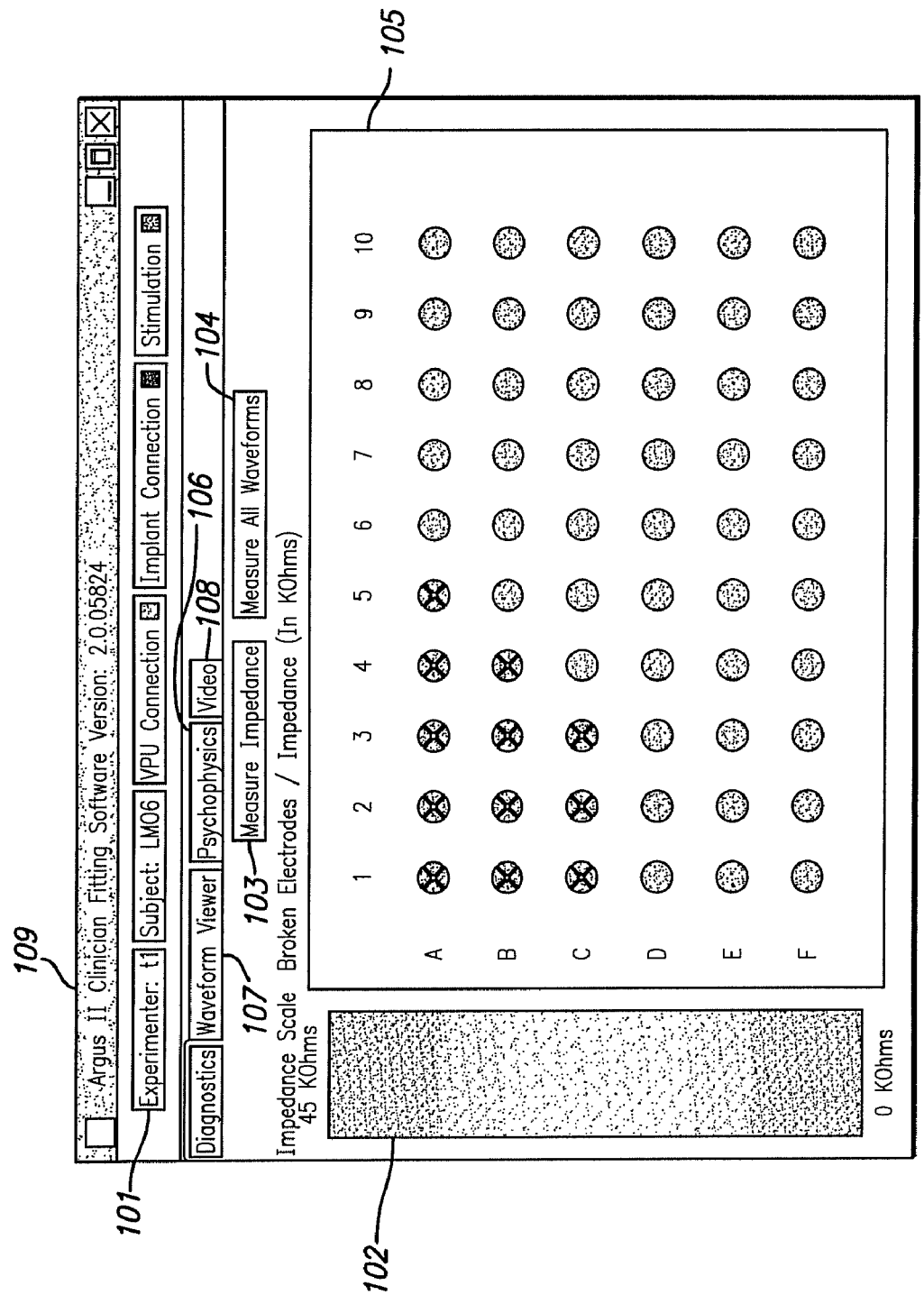
FIG. 14 shows a diagnostics computer screen.

The Diagnostic Module Screen 109 shown in FIG. 14 may contain: 1) Session Information 101 displaying (a) Experimenter (User) ID, (b) Subject ID, (c) VPU Connection identifying the status of the connection of the VPU to the FS, (d) Implant Connection identifying the status of the connection of the implant to the FS, and (e) Stimulation identifying the status of stimulation (i.e., whether or not stimulation is occurring); 2) Measure Impedance 103 for measuring impedance for the electrodes; 3) Measure All Waveforms 104 for measuring waveforms for the electrodes; 4) Broken Electrodes/Impedance (in kOhms)–6×10 Electrode Grid 105 representing each of the implant electrodes. The view of the electrodes is from the perspective of the subject. The electrodes shown as "⊗" are designated as broken/shorted. When measuring impedance, the values will appear directly under each represented electrode. Stimulation should not occur on electrodes designated as broken; and 5) Impedance Scale 102 for impedance that ranges from 0 to 45 kOhms.

Figure 15:
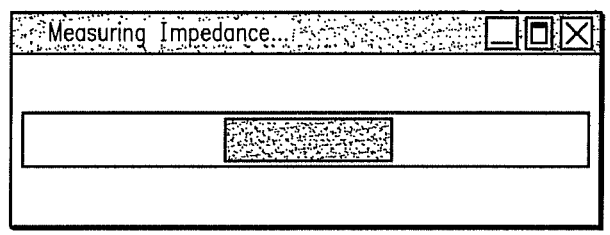
FIG. 15 shows a 'Measuring Impedance' message box.
Figure 16:
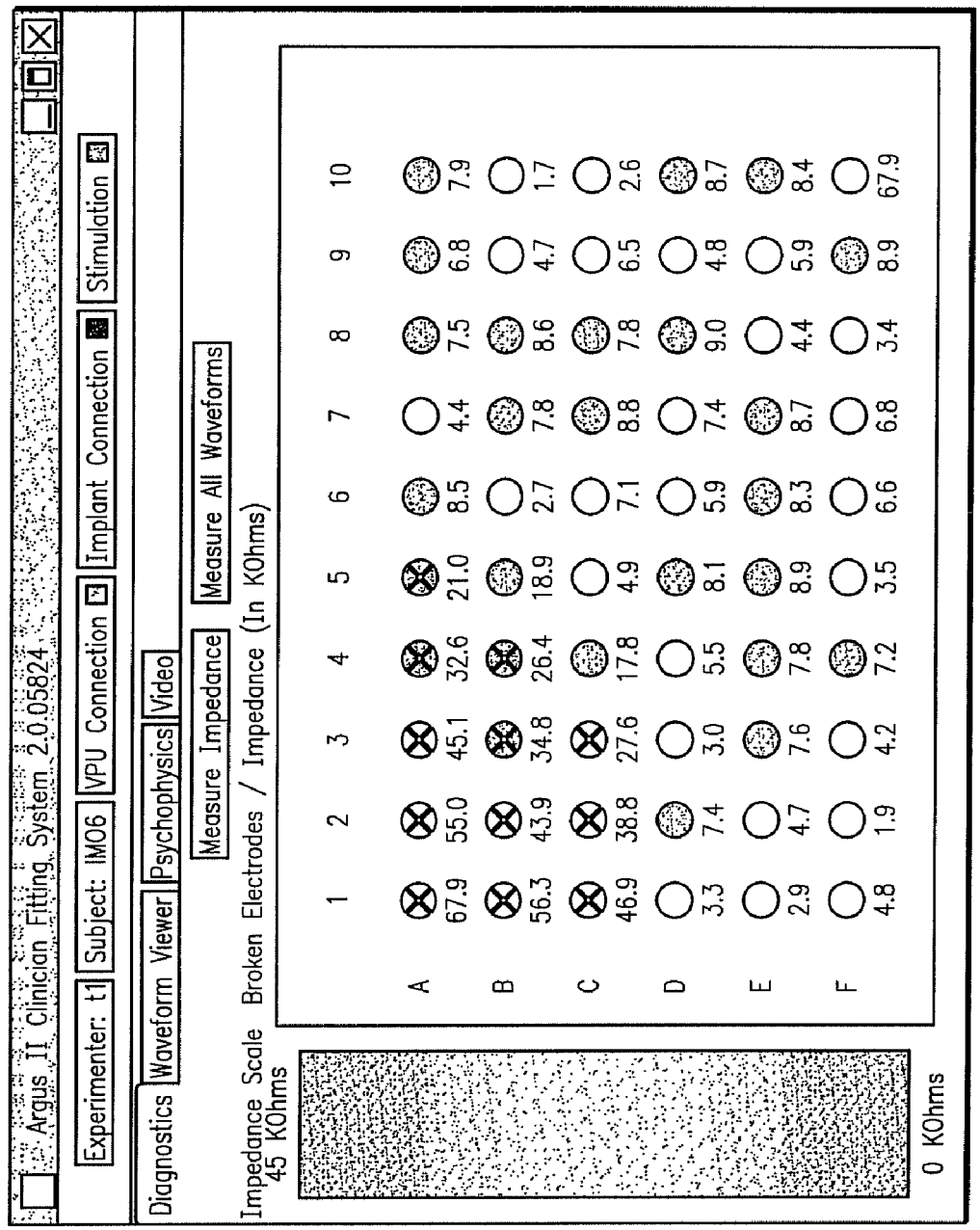
FIG. 16 shows a computer screen indicating impedance values.

Clicking on the Measure Impedance 103 will measure impedance of the electrodes and a message box shown in FIG. 15 may be used to indicate the progress of obtaining impedance measurements. Once the impedance measurements are completed, the impedance values (in kOhms) will be displayed as shown in FIG. 16 under each represented electrode. Each of the electrodes may be color coded based on where the impedance value falls within the impedance scale from 0 to 45 kOhms of the Impedance Scale 102. The impedance values for the subject may be automatically stored in a file marked for transfer on the FS laptop 10.

Figure 17:
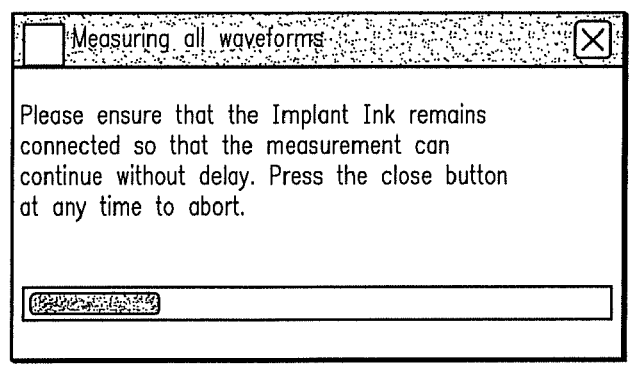
FIG. 17 shows a message box indicating progress of waveform measurements.

To measure waveforms, Clicking on "Measure All Waveforms" 104 will measure waveforms of the electrodes and a message box shown in FIG. 17 may be used to indicate the progress of the waveform measurements. Once the measurements are complete, the waveform information may be stored in a file marked for transfer on the FS laptop 10. The waveforms for each of the electrodes can be viewed from the Waveform Viewer 107.

Figure 18:
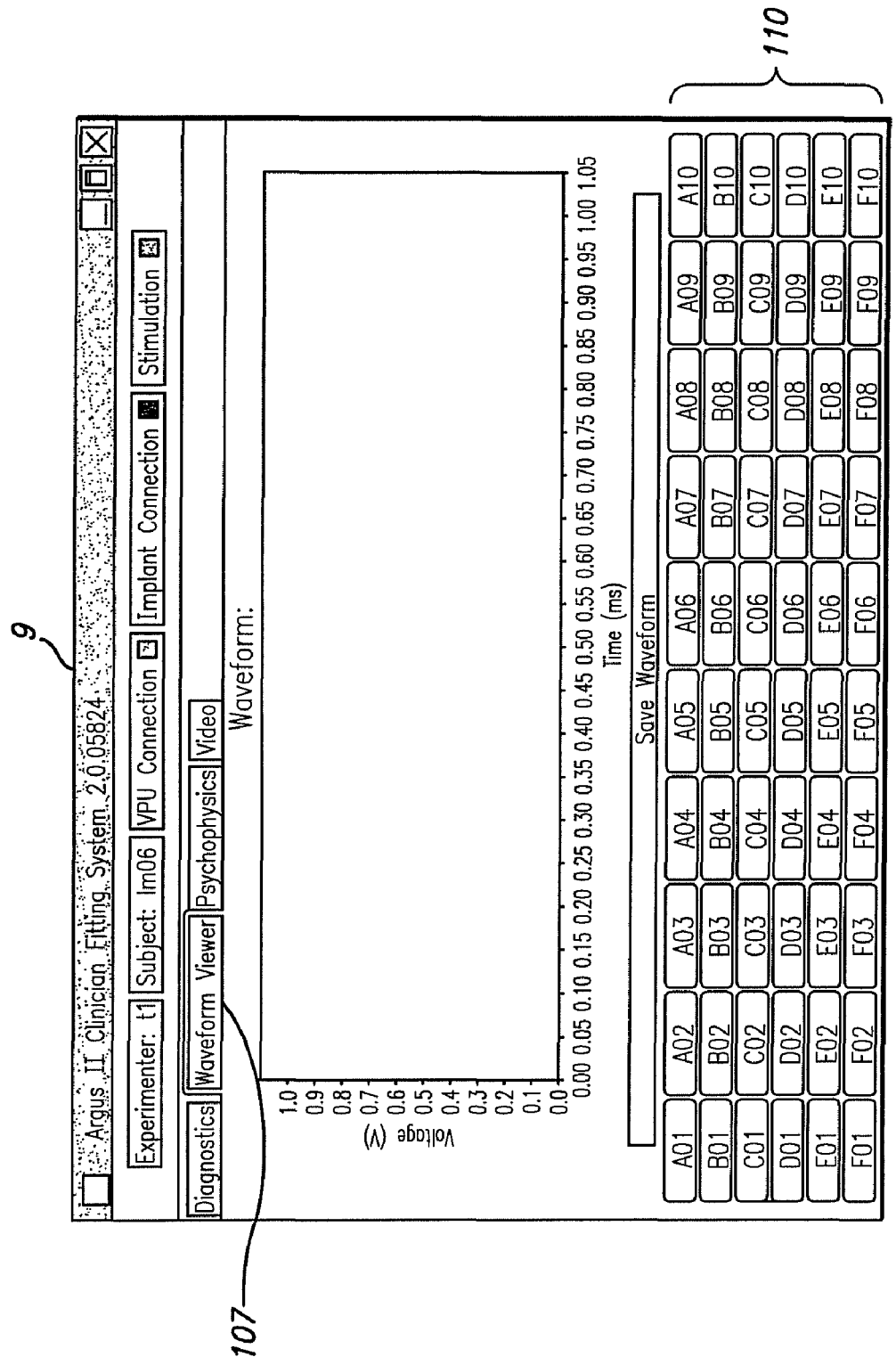
FIGS. 18 and 19 show waveform computer screens.
Figure 19:
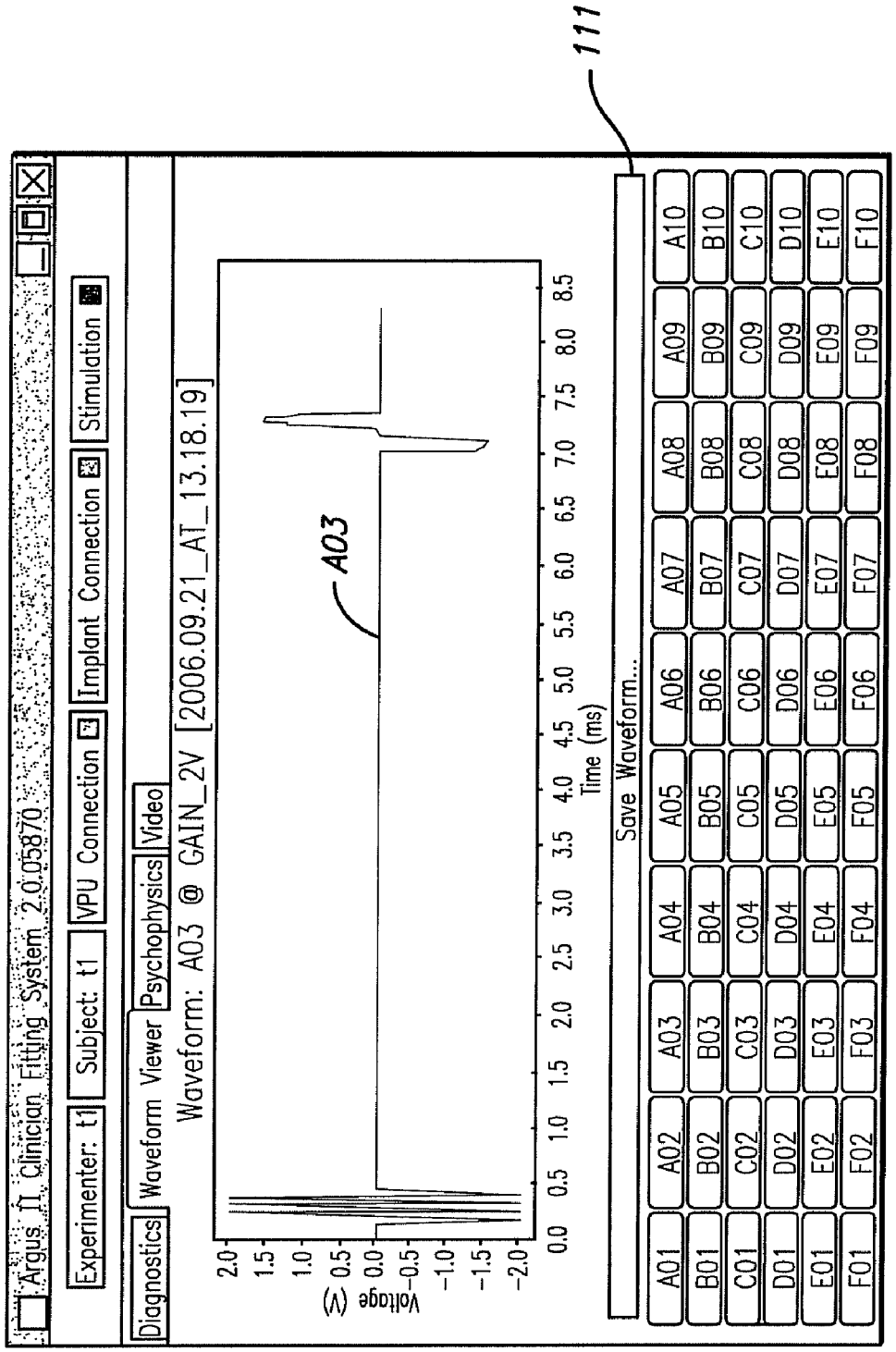

The Waveform Viewer 107 shown in FIG. 18 is a utility that may be used to measure and view the waveform of a selected electrode. From the list of the electrodes at the bottom of the screen (displayed in a 6×10 configuration 110 with their Cartesian coordinates), a specific electrode for which to measure the waveform may be selected. Upon selection of the electrode, the VPU 20 will record the waveform and the information will be sent to the FS so that the waveform data may be presented on the screen as shown in FIG. 19 in which, for example, the waveform of A03 is measured during stimulation. By right clicking on the mouse, it may be possible to zoom in and zoom out on the displayed waveform. The waveform may be saved by clicking on the Save Waveform button 111.

The video application 108 may be used to load a video configuration file to the VPU 20 to allow the VPU 20 to be used properly in Stand-Alone mode. The video configuration file provides the instructions for the stimulation that each electrode will deliver based on the video stream captured by a camera located on the Glasses 5.

The video configuration files may be in a comma separate value (.csv) format. The video configuration file may define the following: 1) Comment: Begin a line with "#," to insert a comment on any line. These lines will be displayed in the message window in the video module of CFS when a particular video configuration file is loaded, 2) Template format: The VPU 20 and FS accommodates certain formats for a video configuration file. The format used must be specified in the file, 3) Current amplitude range: Specify the current amplitude range (one value for all electrodes), 4) Stimulation frequency: Specify the frequency at which stimulation will occur (one value for all electrodes), 5) Pulse timing profile specification: Six pulse timing profiles should be specified. These six profiles form a library from which individual profiles can be chosen for creating the anodic and cathodic pulses for each electrode, 6) Brightness map: Specify the brightness map for each electrode, 7) Cathodic and anodic profiles for each electrode: From the library of pulse timing profiles, specify a timing profile for the cathodic and anodic pulses for each electrode, and 8) Spatial map: Specify the spatial map for each electrode (x, y coordinates). Multiple video configuration files may be created for each subject.

Figure 20:
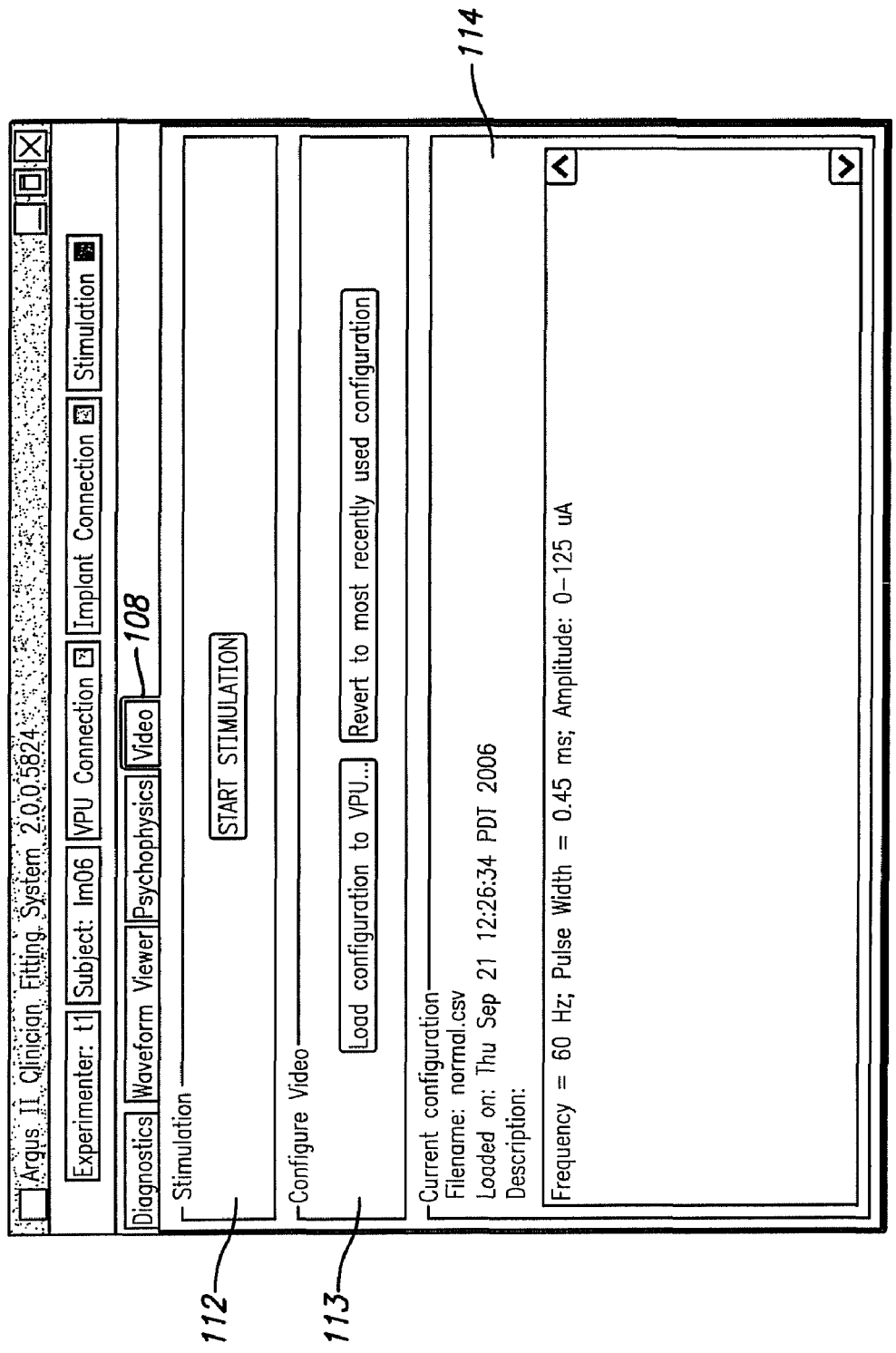
FIG. 20 shows a computer screen with different subsections of a 'video' application.

The Video 108 may consist of three sub-sections as shown in FIG. 20. They may be a 'Stimulation' section 112, a 'Configure Video' section 113, and a 'Current Configuration' section 114. Within the 'Stimulation' section 112 is the button to start stimulation of the subject with the video configuration file downloaded to the VPU 20. The 'Configure Video' section 113 has two buttons: "Load Configuration to VPU" and "Revert to most recently used configuration." The "Load Configuration to VPU" may be used to load the desired video configuration file to the VPU 20. The "Revert to most recently used configuration" may be used to bring up the video configuration file that was last used for stimulation. The 'Current Configuration' section 114 may be used to display the resident video configuration on the VPU 20 by providing the file name, the date it was loaded, and a description of the file (if applicable).

Figure 21:
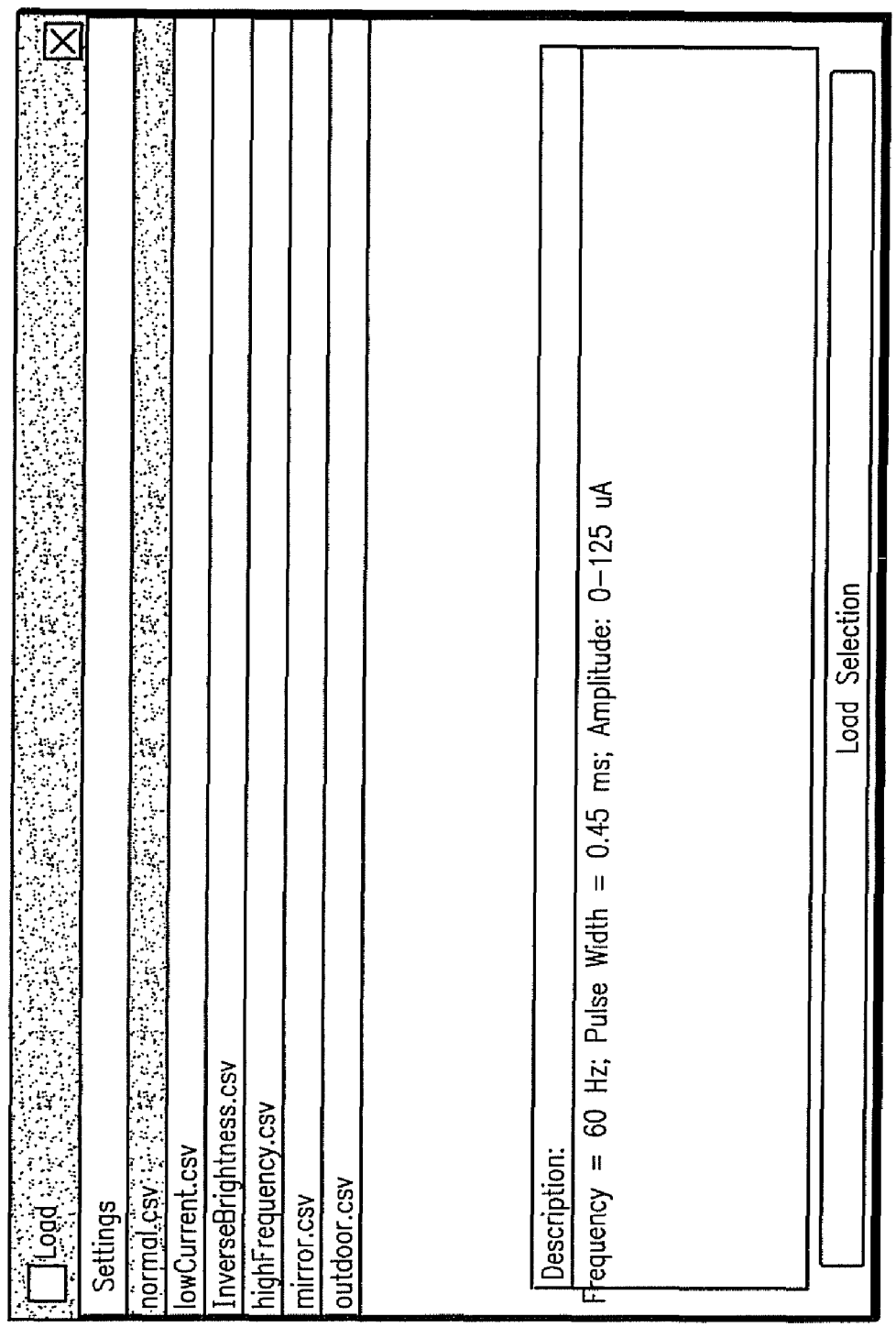
FIG. 21 shows a 'Load' computer screen.

To load a different video configuration file to the VPU 20, one may use that "Load configuration to the VPU" option to bring up a 'Load' screen shown in FIG. 21 to show a listing of video configuration files. Clicking on a configuration file in FIG. 21 will display a description of that selected file in the description box provided that the description was included as part of the video configuration file. When the desired video configuration is located, a "Load Selection" option in FIG. 21 may be used to load file to the VPU 20. The file name, along with the load date and time will be displayed in the "Current configuration" section 114 on the Video Screen in FIG. 20. The VPU 20 may be set up to not download any file that does not meet the necessary safety requirements for stimulation.

Figure 22:
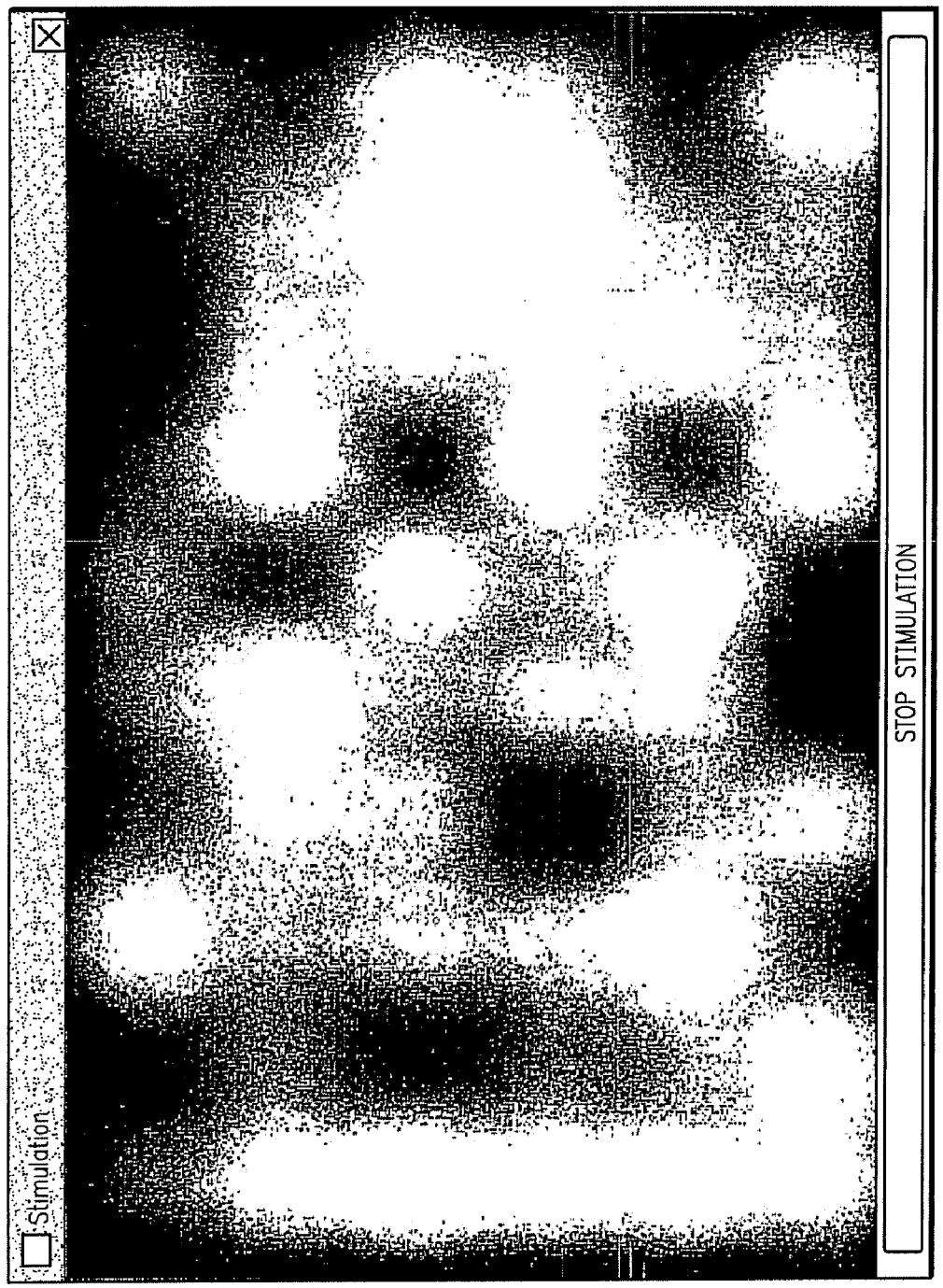
FIG. 22 shows a 'stimulation' computer window.

Once a desired video configuration file is loaded, a stimulation of the subject may be performed using START STIMU- LATION in section 112 of FIG. 20. A stimulation window shown in FIG. 22 may be used to display a pixelized representation in a 6×10 grid of the filtered image displayed to the subject. A 12×20 pixelized image, which is twice the resolution of the filtered image, can also be displayed.

The Psychophysical Test System (PTS) is part of the Retinal Stimulation System 1 as it is intended to be used to facilitate fitting a subject by characterizing the subject's perceptual responses to electrical stimuli. The results from the psychophysical experiments may be accumulated, evaluated and used to determine the stimulation parameters of the VPU 20 during video stimulation.

Additionally, PTS may provide a framework for researchers and investigators to develop customized psychophysical experiments. PTS may comprise four ways to execute psychophysical experiments: 1) Threshold with Method of Adjustment, 2) Brightness Matching, 3) Direct Stimulation, and 4) Clinician-Designed Research Experiments. Each being described in detail below.

The Threshold with Method of Adjustment may be used to determine the stimulation current threshold for an individual electrode (i.e. the stimulation level at which a percept is first seen). The user interface allows the experimenter to (1) configure the experiment, including which electrodes to test, how many trials are tested per electrode and other stimulation timing parameters, (2) preview the stimulation waveform, (3) capture subject responses, and (4) view experiment results on the screen as the test progresses, and save the results.

In this test, the subject will be stimulated on one of the test electrodes. The subject may use the Patient Input Device (Jog Dial) 55 to increase or decrease the stimulation current amplitude on the selected electrode after each stimulation. To indicate the threshold, the subject may press down the Jog Dial 55 when perception occurs. The Results screen displays the threshold and another test electrode is tested. This continues until all selected electrodes are tested for a number of trials, as configured by the experimenter. All stimulation parameters may be recorded by the Fitting System in the psychophysics log.

The Brightness matching may be used to determine the relationship between electrode stimulation current and the perceived brightness. These data are analyzed to determine the current amplitudes required to elicit the same perceived brightness for each electrode in the array. The user interface allows the experimenter to (1) configure the experiment, including which electrodes to test, which electrode and what amplitude to use as a reference, how long to wait between the two stimuli, the number of trials per test electrode, and other stimulation timing parameters, (2) preview the stimulation waveform, and (3) view the stimulation and subject response as the test progresses.

In each trial, the subject may be stimulated with two stimuli, one on the test electrode and one on the reference electrode (The order of the stimuli is random). The subject may use the keys on the Patient Input Device (Tablet) 50 to signal which of the two temporal intervals contains the brighter stimulus. This process will continue until each of the selected electrodes has been tested for a number of trials, as configured by the experimenter.

Using Direct Stimulation, an experimenter is able to (1) design a stimulation wave form on a single or multiple electrodes and (2) conduct manual testing on a single or multiple electrodes. During the use of Direct Stimulation, no subject response is automatically logged in FS.

The PTS System, may, for example, also have MATLAB software installed to allow clinicians to develop their own customized psychophysical experiments for research purposes. These experiments may be used for research purposes.

Figure 23:
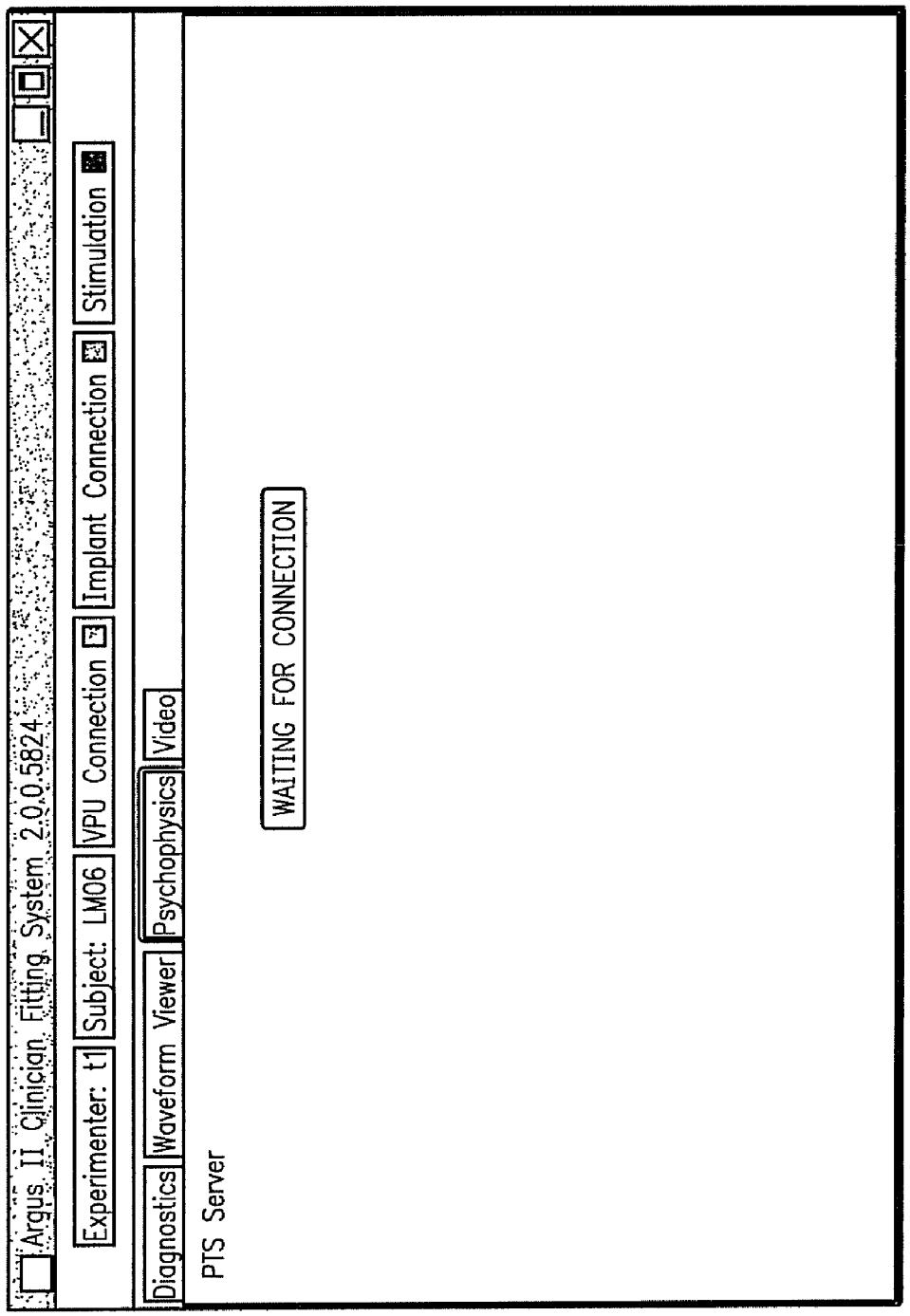
FIG. 23 shows a 'waiting for connection' message box.

The following provides instructions for running the Threshold Method of Adjustment, Brightness Matching, and Direct Stimulation Psychophysical experiments. By selecting the Psychophysics tab 106 of FIG. 14, FS will attempt to connect with PTS. "WAITING FOR CONNECTION," as shown in FIG. 23 may be displayed indicating that FS is waiting for a connection with PTS.

Figure 24:
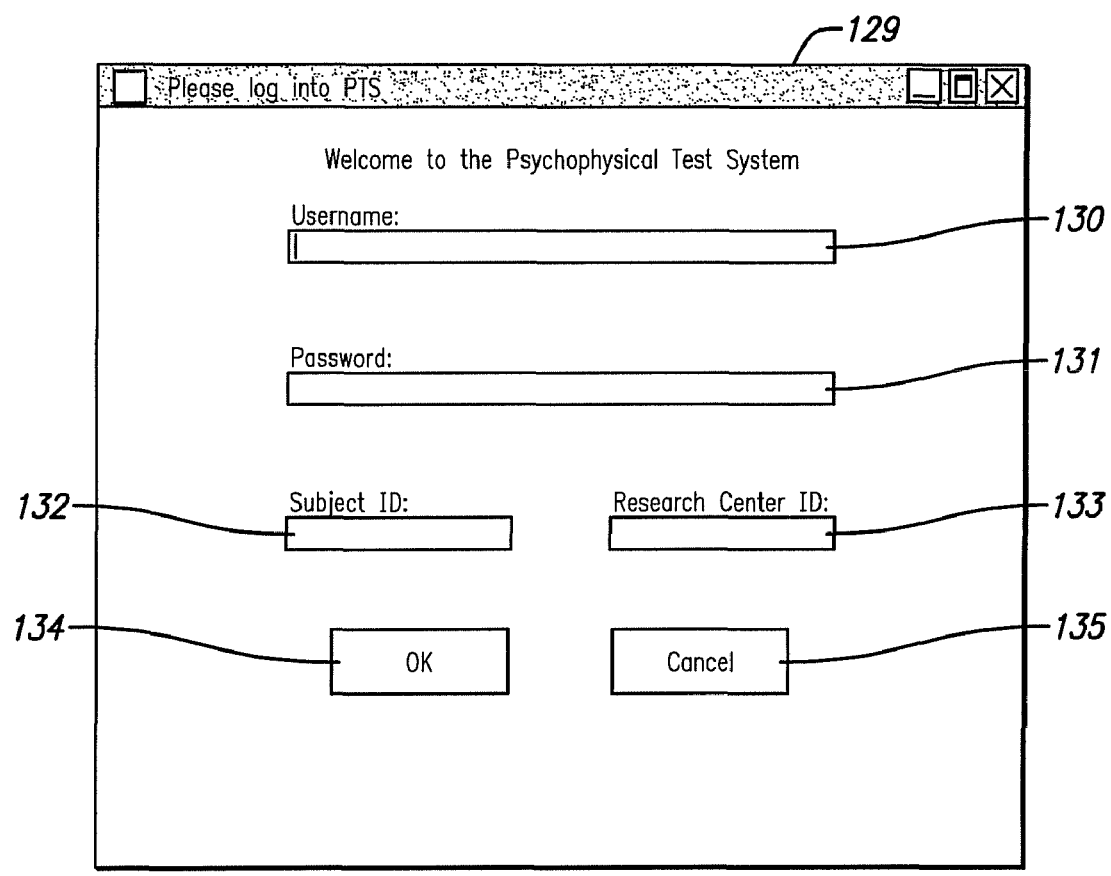
FIG. 24 shows a computer window requesting specific information.

A window 129 shown in FIG. 24 will appear on the PTS laptop 30 requesting Username 130, Password 131, and Subject ID 132 and the site specific Research Center ID 133. 'OK' 134 may be used to proceed to the Psychophysical Test System Main Menu and 'Cancel' 135 may be used to quit the session.

Figure 25:
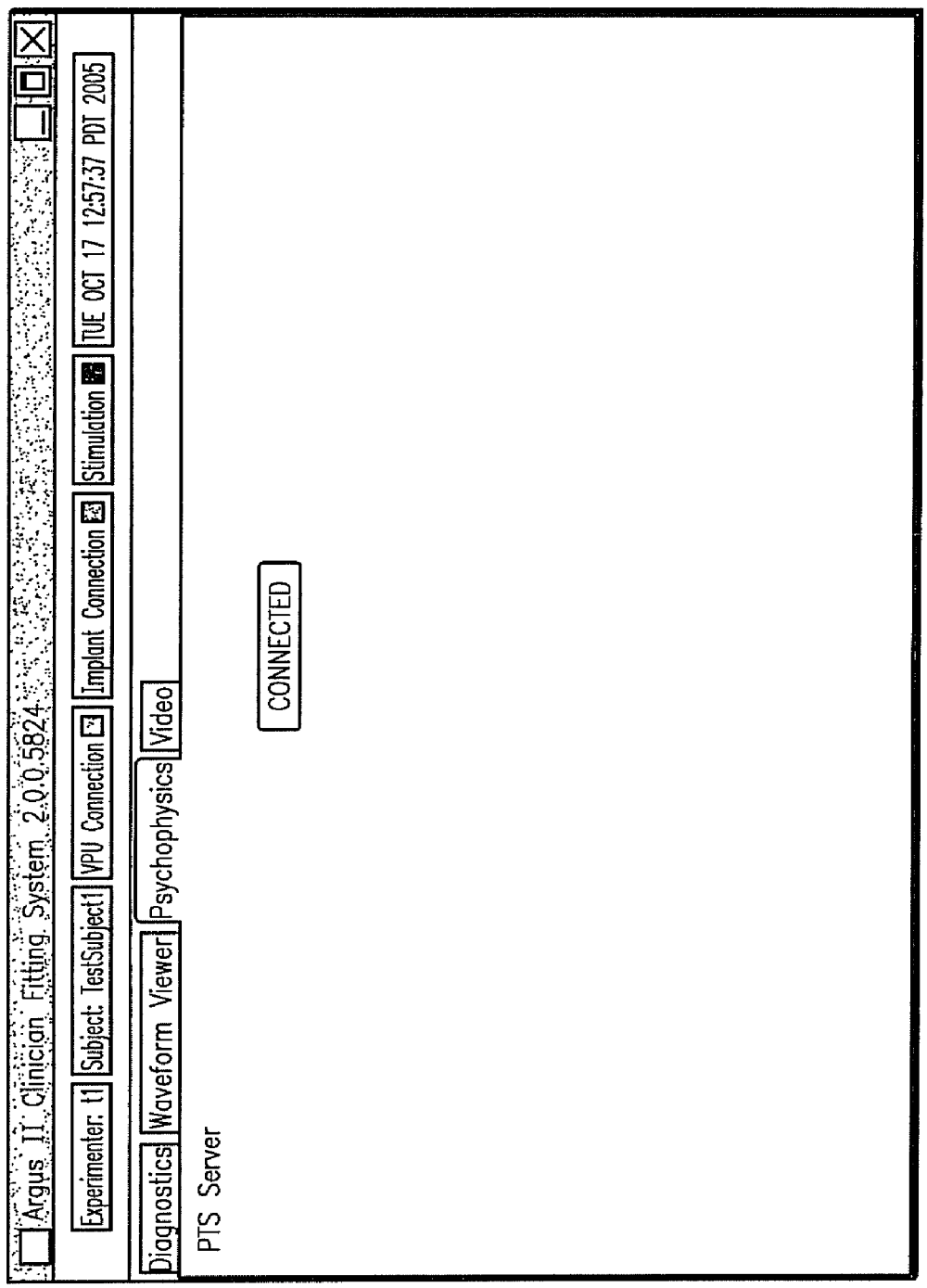
FIG. 25 shows a 'connected' message box.

If 'OK' 134 is selected, the PTS Server screen on the FS Laptop 10 should display "CONNECTED", as shown in FIG. 25, to indicate that a connection has been successfully established between the FS and PTS.

Figure 26:
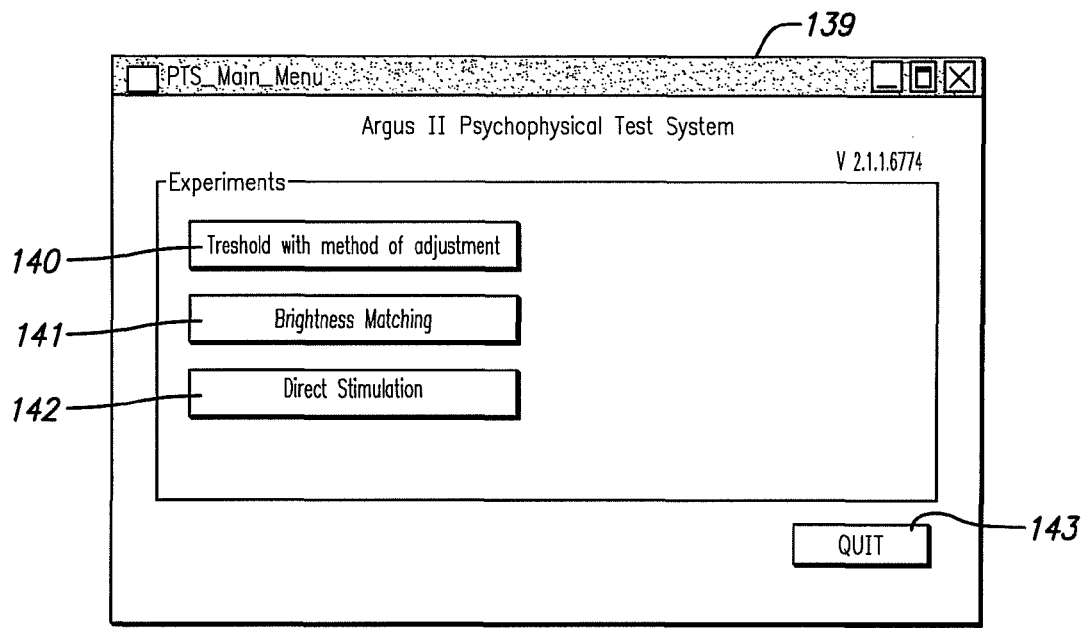
FIG. 26 shows a Psychophysical Test System (PTS) main screen.

The Psychophysical Test System (PTS) main screen 139, shown in FIG. 26, has four options 1) 'Threshold with method of adjustment' 140, 2) 'Brightness matching' 141, 3) 'Direct Stimulation' 142, and 4) 'Quit' 143.

Next, a way of conducting a threshold measurement using the method of adjustment will be described.

Figure 27:
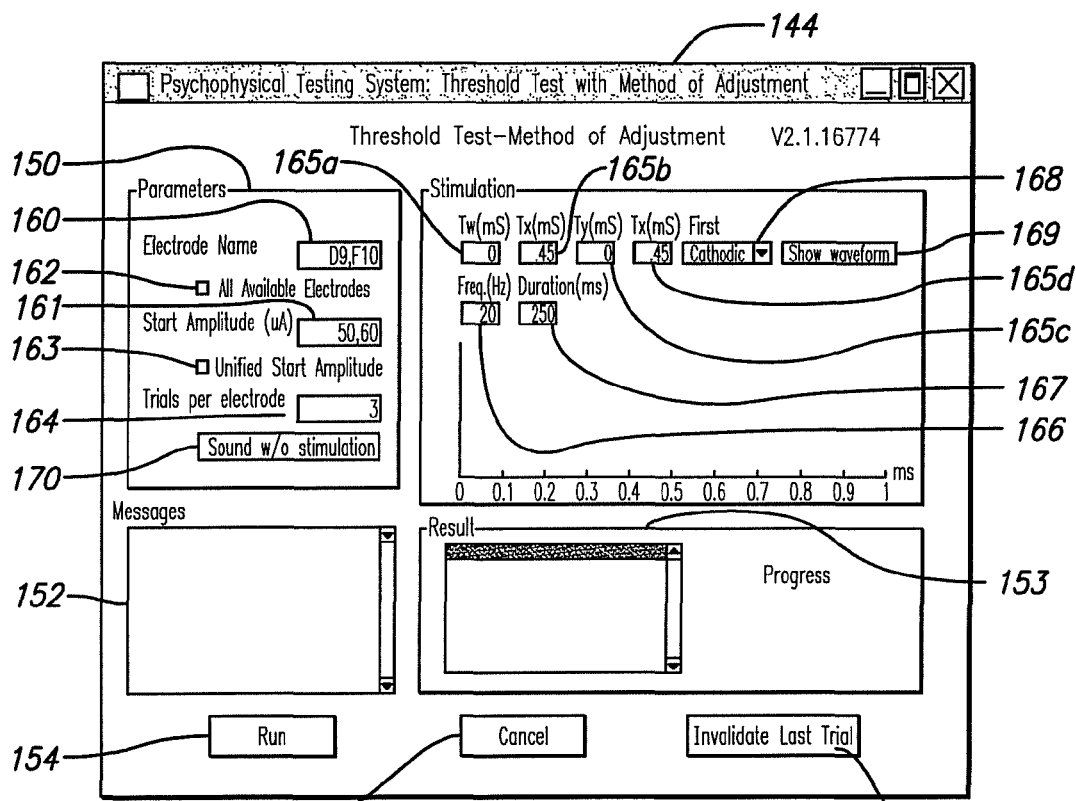
FIG. 27 shows a 'Threshold with Method of Adjustment' screen.

A 'Threshold with Method of Adjustment' screen 144 shown in FIG. 27 appears when the 'Threshold Method of Adjustment' button 140 is selected from the 'PTS Main Menu' screen 139. The 'Threshold with Method of Adjustment' screen 144 may contain:

1) a 'Parameters' panel 150 for experiment parameters that require configuration in order to execute an experiment, 2) a 'Stimulation' panel 151 for stimulation parameters that require configuration in order to execute an experiment;

3) a 'Message' panel 152 for messages that may require the experimenter's attention during the testing. There are two types of messages than can be displayed during a test session: (a) Unknown key pressed—This message is generated if the subject presses an unknown key during the test, and (b) Maximum or minimum amplitude reached—This message is generated if the maximum/minimum current amplitude is reached (as allowed by the maximum charge per phase safety limit) and the subject continues to turn the jog dial to increase/decrease the amplitude. A loud sound may also be emitted to alert the experimenter and the subject;

4) a 'Result' panel 153 for displaying electrodes that are currently under test, stimulation amplitude and previously recorded thresholds in this experiment;

5) a 'Run' button 154 to start to run the threshold with method of adjustment experiment. The program will check the parameters entered against the safety limits and the experimenter will have a chance to correct them if so;

6) a 'Cancel' button 155 to cancel the current running experiment; and 7) an 'Invalidate Last Trial' button 156 to invalidate the last found threshold if the subject pushed the jog dial by accident.

Configuration parameters may be entered for the experiment as described below with reference to FIG. 27.

The names of electrode(s) whose thresholds are to be measured during testing may be entered in the 'Electrode Name' window 160 of the 'Parameters' panel 150. One may select all the electrodes by selecting the 'All Available Electrodes' window 162 of the 'Parameters' panel 150 or one may select only certain electrodes from the grid shown in a Table 1 below.

TABLE 1

| A1 | A2 | A3 | A4 | A5 | A6 | A7 | A8 | A9 | A10 |
|----|----|----|----|----|----|----|----|----|-----|
| B1 | B2 | B3 | B4 | B5 | B6 | B7 | B8 | B9 | B10 |
| C1 | C2 | C3 | C4 | C5 | C6 | C7 | C8 | C9 | C10 |
| D1 | D2 | D3 | D4 | D5 | D6 | D7 | D8 | D9 | D10 |
| E1 | E2 | E3 | E4 | E5 | E6 | E7 | E8 | E9 | E10 |
| F1 | F2 | F3 | F4 | F5 | F6 | F7 | F8 | F9 | F10 |

The starting stimulation amplitude(s) (μA) for each of the test electrodes may be entered in the 'Start Amplitude' window 161 of the 'Parameters' panel 150. A 'Unified Start Amplitude' window 163 of the 'Parameters' panel 150 may be checked to enter a single Start Amplitude for all electrodes.

The number of threshold measurements to be made on each electrode may be entered in the 'Trials per electrode' window 164 of the 'Parameters' panel 150.

Figure 28:
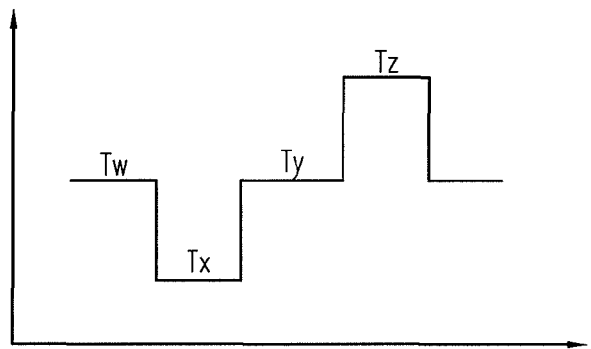
FIG. 28 shows a waveform related to FIG. 29.

The pulse Width (ms) may be entered into windows 165a-d of the 'Stimulation' panel 151. The desired time between start of the effective stimulation window and initiation of the first phase may be entered into a Tw window 165a. The duration of the first phase may be entered into a Tx window 165b. The desired time between the end of the first phase and the beginning of the second phase may be entered into a Ty window 165c. The duration of the second phase may be entered into a Tz window 165d. FIG. 28 depicts a waveform of the numbers entered into windows 165a-d.

Figure 29:
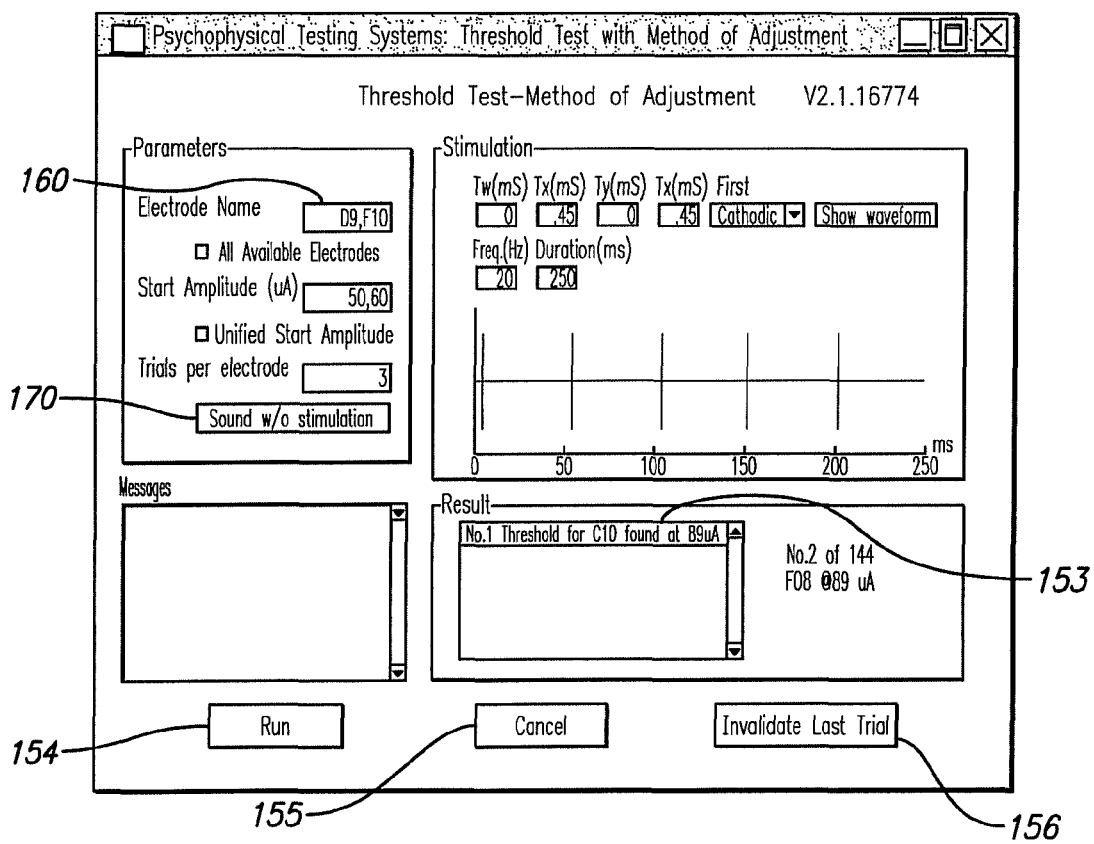
FIG. 29 shows a 'Threshold Test' computer screen.

The frequency of how many times per second the waveform shown in FIG. 28 will be repeated may be entered into a 'Frequency' window 166 of the 'Stimulation' panel 151. The desired length of each stimulation in milliseconds (i.e. the length of stimulation at a given test amplitude) may be entered into a 'Duration' window 167 of the 'Stimulation' panel 151. Selection of whether the first phase is negative (cathodic) or positive (anodic) current may be performed using 'First' window 168 of the 'Stimulation' panel 151. A 'Show waveform' button 169 may be used to produce a graph that plots the waveform of the complete stimulus for a trial. A 'Sound w/o stimulation' button 170 may be used to generate a sound (the same as the one heard when stimulation is delivered) without actually delivering stimulation. Once all configuration parameters have been entered, the experimenter has the option to press the 'Show Waveform' button 169 prior to initiating the experiment to check the parameters to produce a graph that plots the waveform of the complete stimulus for a trial as shown in FIG. 29. A 'Run' button 154 may be used to proceed with the experiment.

Figure 30:
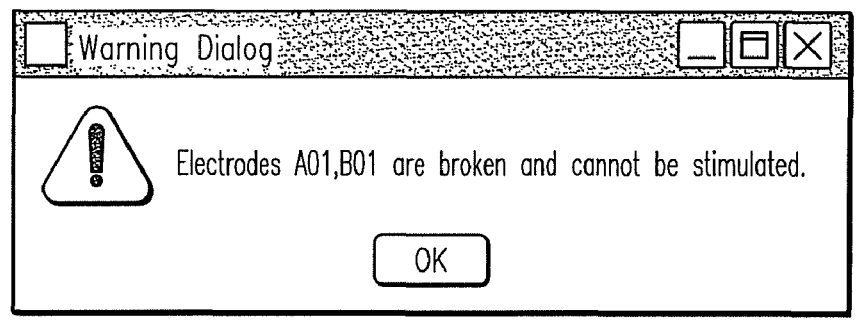
FIGS. 30 and 31 show warning dialog message boxes.
Figure 31:
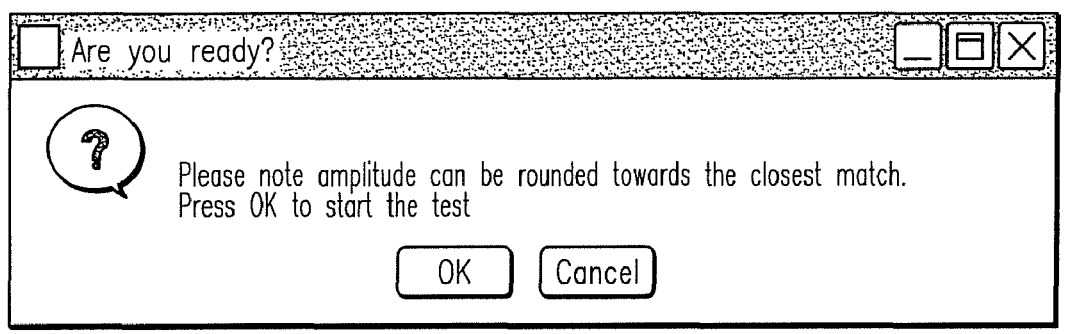

After the 'Run' button 154 or 'Show Waveform' button 169 are activated, the parameters may be checked against safety requirements of the system. If any of the parameters violates safety limits, a message box may be displayed and the experimenter will need to change the configuration parameters. Common errors may include broken/shorted electrodes and start amplitudes which exceed maximum charge per phase limit. For example, if any of the chosen electrodes are already deemed broken/shorted, a popup message shown in FIG. 30 may be displayed on the screen. If no safety violations are found, a popup message shown in FIG. 31 will appear. If the requested pulse amplitude cannot be generated by the VPU 20, the closest value will automatically be used. The value will appear in the results section discussed below.

After each stimulus presentation, the subject may turn the jog dial 55 to the right to increase stimulation amplitude, or may turn the jog dial 55 to the left to decrease stimulation amplitude. The subject may increase or decrease the stimulation level until he/she has determined their threshold (i.e. the minimum stimulation amplitude for seeing the stimulation.) The subject may signal the threshold for that electrode by pressing down on the Jog Dial 55. If multiple electrodes are tested, the electrodes may be tested in random order.

Figure 32:
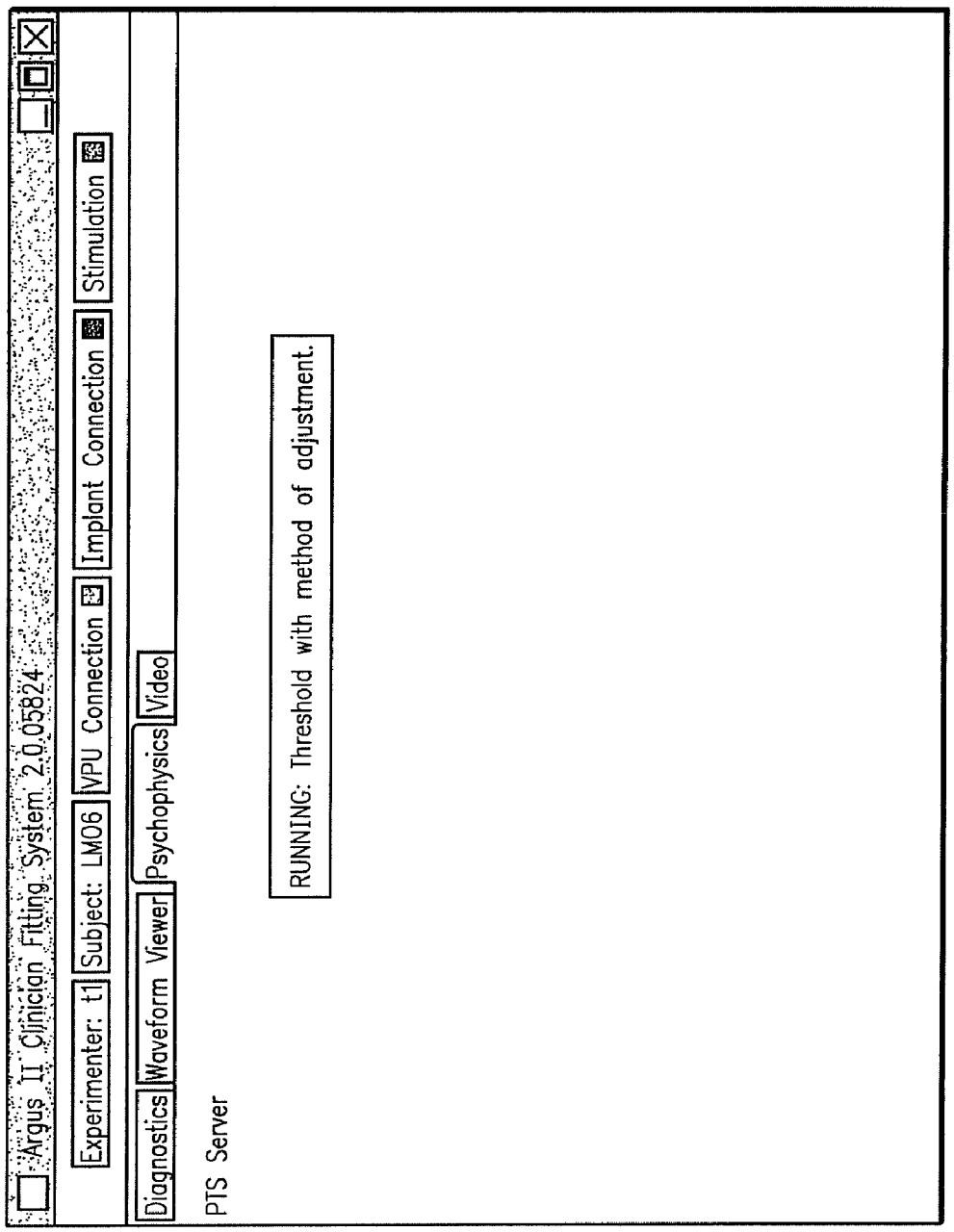
FIG. 32 shows a 'RUNNING: Threshold with method of adjustment' message.

During a Threshold with Method of Adjustment experiment, the PTS Server screen on the FS Laptop 10 may display 'RUNNING: Threshold with method of adjustment' is shown in FIG. 32. At any time during the experiment, the experimenter can click the 'Sound w/o stimulation' button 170 to generate a stimulation sound without actually delivering stimulation to the subject.

If for any reason, the experimenter determines that the last threshold measurement is invalid (e.g. the subject pressed down the jog dial 55 accidentally), the experimenter can click on the 'Invalidate Last Trial' button 156 to invalidate that trial. This may be set up to invalidate only the results of the last trial, not the whole experiment. The 'Result' panel 153 will show the trial as "Invalid" and the trial will be repeated in a random order with the remaining electrodes as shown in FIG. 29.

The experiment ends once all of the trials have been completed. In the 'Result' panel 153, the total number of trials and number of finished trials may be displayed throughout the experiment. The 'Cancel' button 155 may be used to stop an experiment prior to the completion of all trials.

Figure 33:
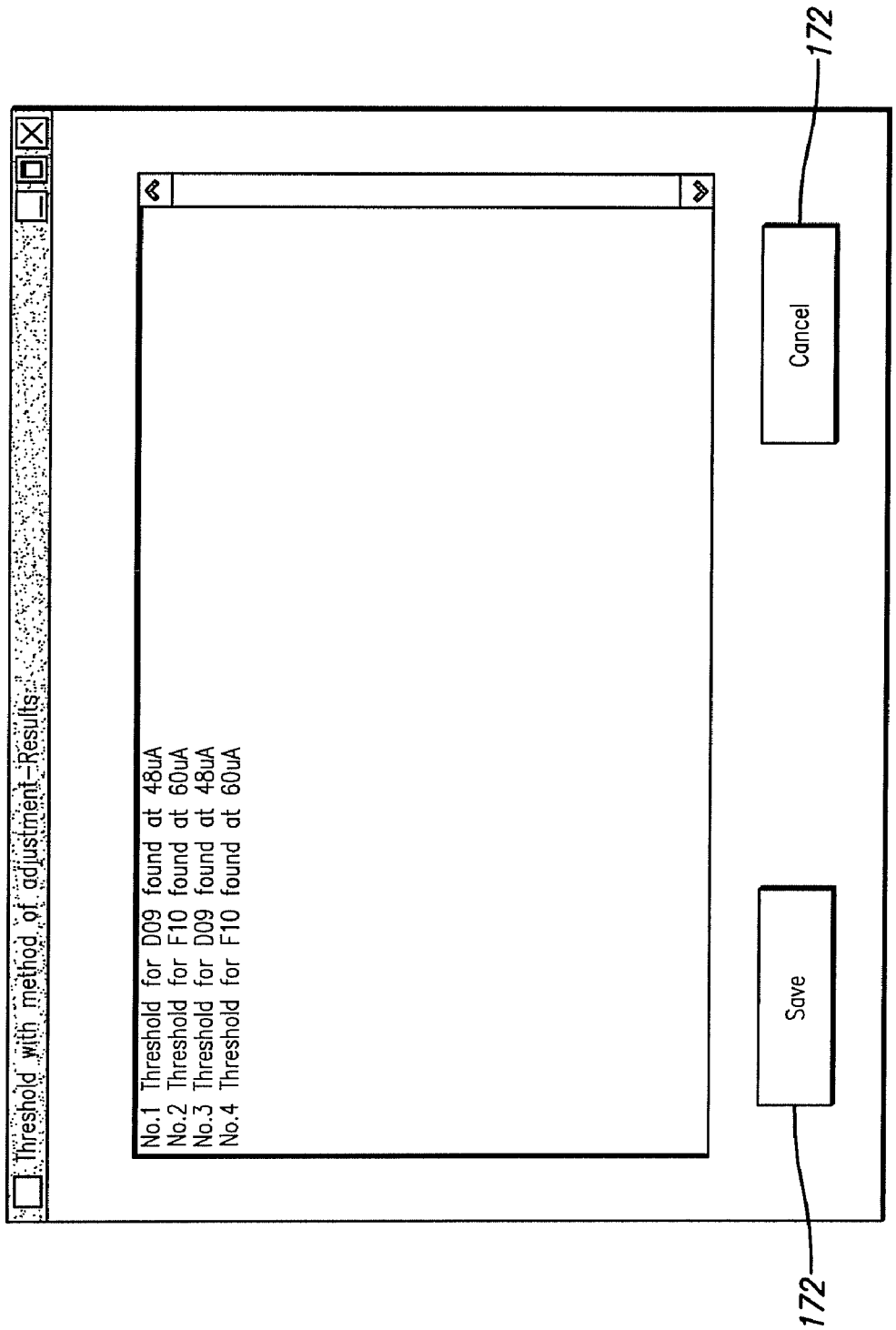
FIG. 33 shows a 'Threshold Test with Method of Adjustment' message box.

At the end of the experiment, the "Threshold with method of adjustment-results" screen shown in FIG. 33 may appear and the experimenter may have the option of saving the results to a hard drive.

Figure 34:
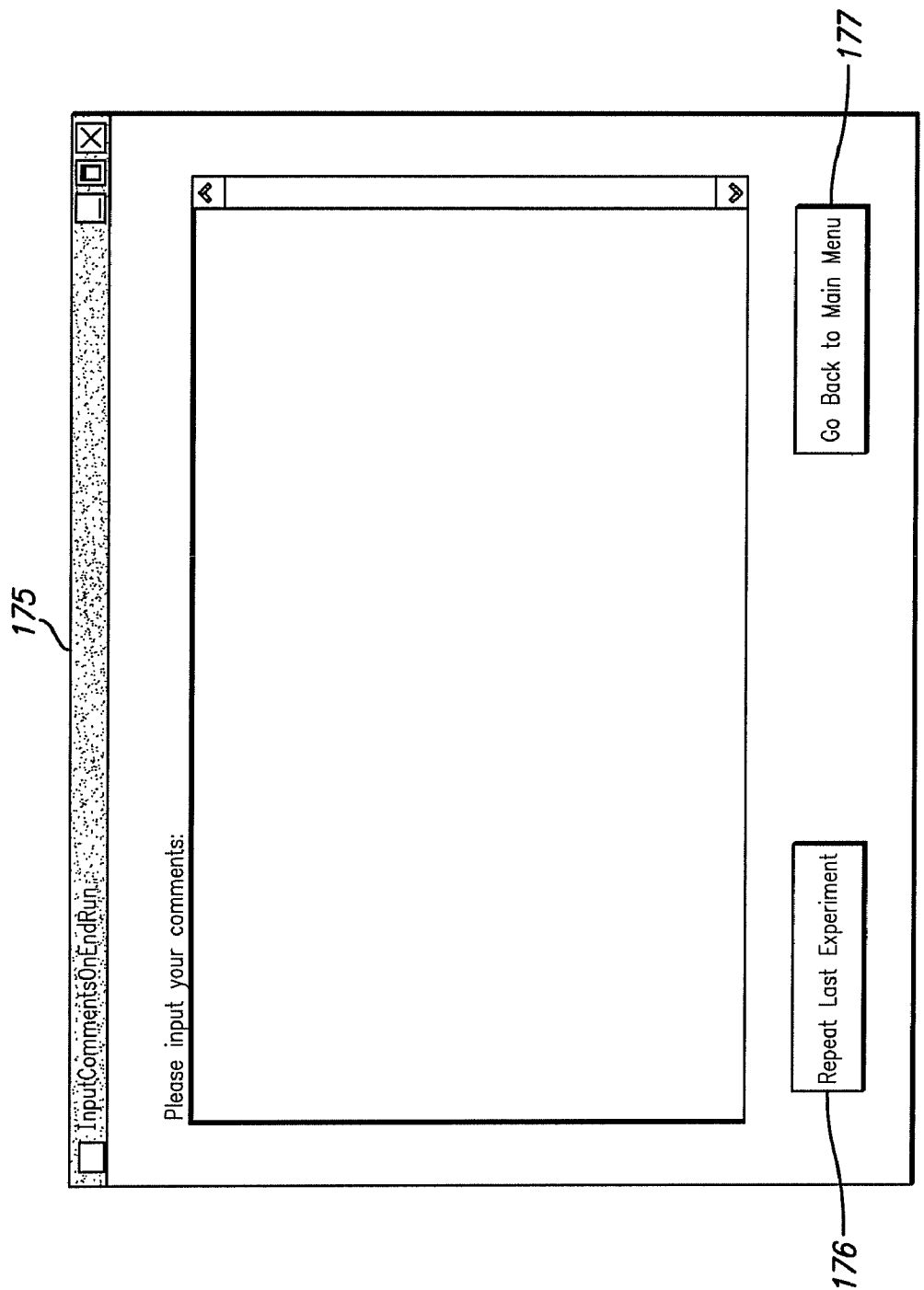
FIG. 34 shows an 'Input Your Comments' message box.

After saving the results and/or canceling, a 'Comment' screen 175 shown in FIG. 34 may be used for comments. The 'Comment' screen 175 contains two buttons, 'Repeat Last Experiment' 176 and 'Go Back to Main Menu' 177. If 'Repeat Last Experiment' 176 is chosen, the experimenter will be returned to the main Threshold Test—'Method of Adjustment' screen 144 of FIG. 27 with the Parameters from the last experiment and the experimenter can modify and repeat the experiment. If 'Go Back to Main Menu' 177, is chosen, the experimenter will be returned to the main PTS menu 139.

Figure 35:
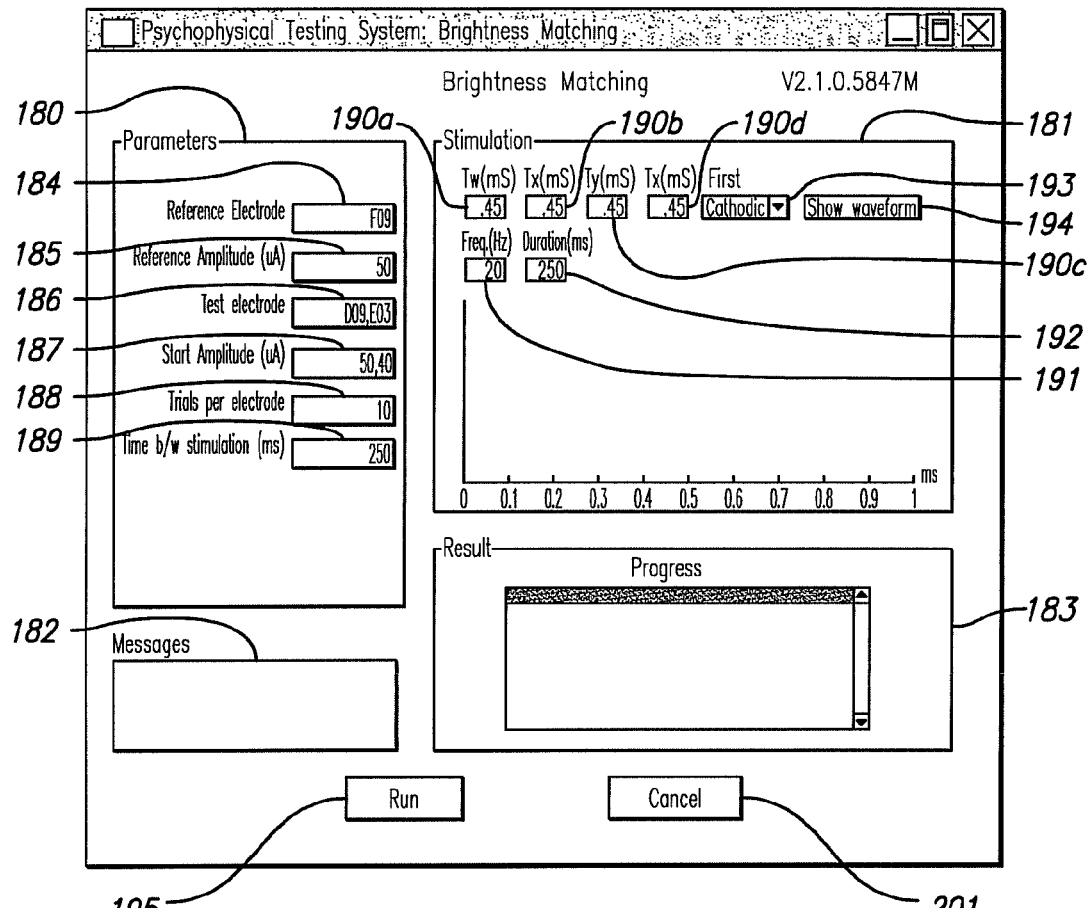
FIG. 35 shows a 'Brightness Matching' computer screen.
Figure 36:
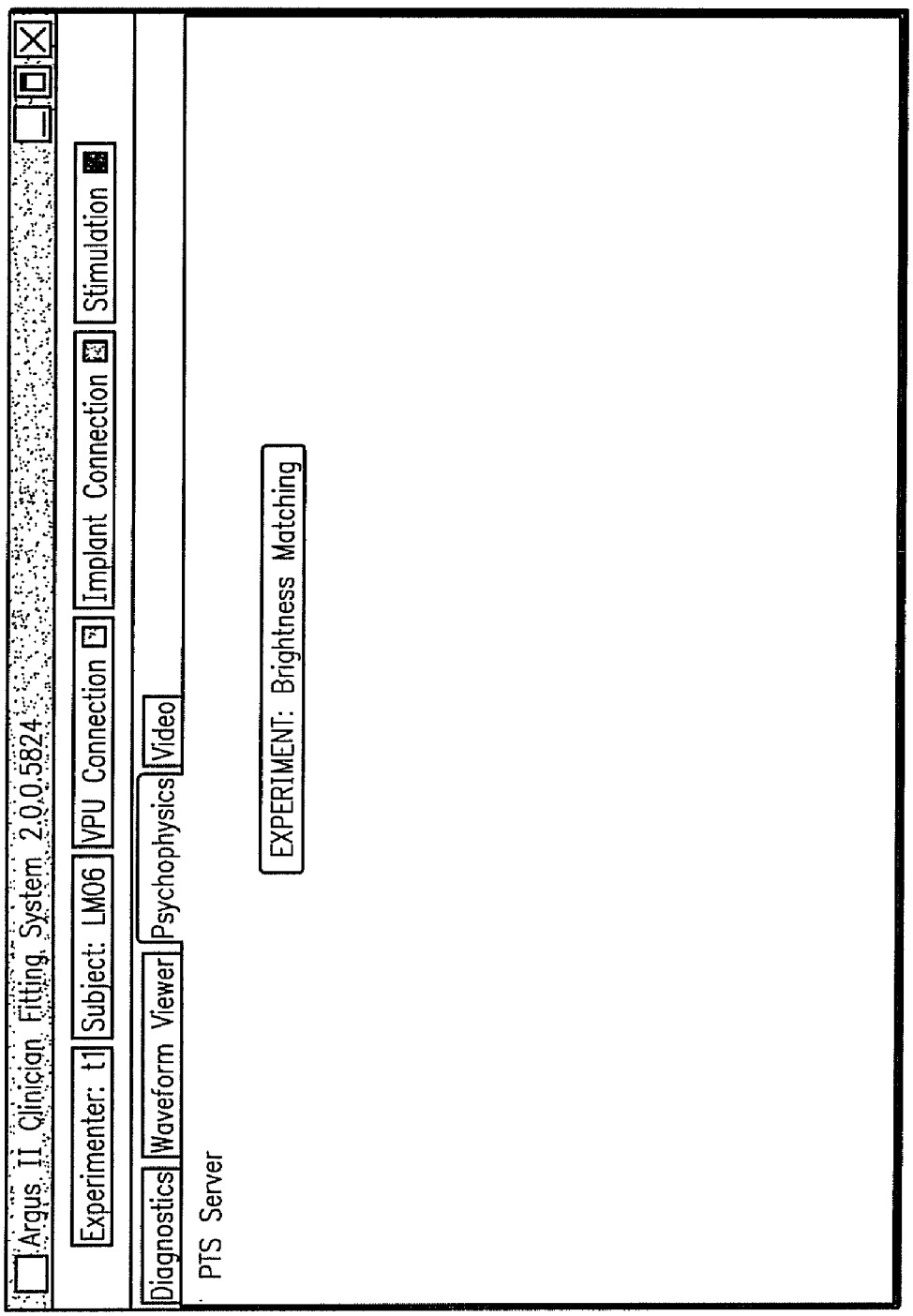
FIG. 36 shows an 'EXPERIMENT: brightness matching' message box.

A 'Brightness Matching' screen 178 shown in FIG. 35 appears when the 'Brightness Matching' 141 button is selected from the 'PTS Main Menu' Screen 139. The 'Brightness Matching' screen 178 may contain 1) 'Parameters' panel 180, 2) 'Stimulation' panel 181, 3) 'Message' panel 182, and 4) 'Result' panel 183. During a Brightness Matching experiment, the PTS Server screen on the FS Laptop 10 may display "EXPERIMENT: Brightness matching" as shown in FIG. 36.

Configuration parameters may be entered for the experiment as described below with reference to FIG. 35.

The name of the standard electrode that will be matched to the brightness of each test electrode may be entered into the 'Reference Electrode' window 184 of the 'Parameters' panel 180. The electrodes may be selected from the grid shown in Table 1 above.

The desired amplitude of the reference electrode that will be matched may be entered into the 'Reference Amplitude' window 185 of the 'Parameters' panel 180.

The desired electrode(s) whose brightness is being varied to match the brightness of the reference electrode may be identified in the 'Test Electrode' window 186 of the 'Parameters' panel 180.

The starting stimulation amplitude (IA) for each of the test electrodes may be entered into the 'Start Amplitude' window 187 of the 'Parameters' panel 180.

The number of brightness matching trials for each electrode may be entered into 'Trials per electrode' window 188 of the 'Parameters' panel 180.

The desired time delay between the reference and test stimuli may be entered into the 'Time between Stimulation' window 189 of the 'Parameters' panel 180.

The Pulse Width (ms) may be entered into windows 190*a-d* of the 'Stimulation' panel 181. The desired time between start of the effective stimulation window and initiation of the first phase may be entered into the Tw window 190*a*. The duration of the first phase may be entered into a Tx window 190*b*. The desired time between the end of the first phase and the beginning of the second phase may be entered into a Ty window 190*c*. The duration of the second phase may be entered into a Tz window 190*d*. FIG. 28 depicts a possible waveform of the numbers entered into windows 190*a-d*.

The frequency of how many times per second the waveform shown in FIG. 28 will be repeated may be entered into a 'Frequency' window 191 of the 'Stimulation' panel 181. The desired length of each stimulation in milliseconds (i.e. the length of stimulation at a given test amplitude) may be entered into a 'Duration' window 192 of the 'Stimulation' panel 181. Selection of whether the first phase is a negative (cathodic) current phase or a positive (anodic) current phase may be performed using a 'First' window 193 of the 'Stimulation' panel 181. A 'Show Waveform' button 194 may be used to produce a graph that plots the waveform of the complete stimulus for a trial. A 'Run' button 195 may be used to proceed with the experiment.

Figure 37:
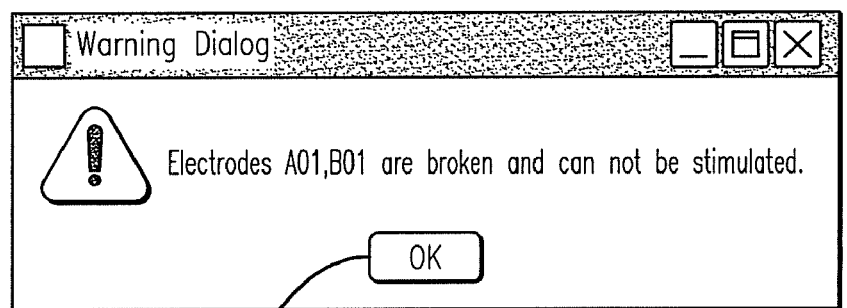
FIGS. 37 and 38 show warning dialog message boxes.
Figure 38:
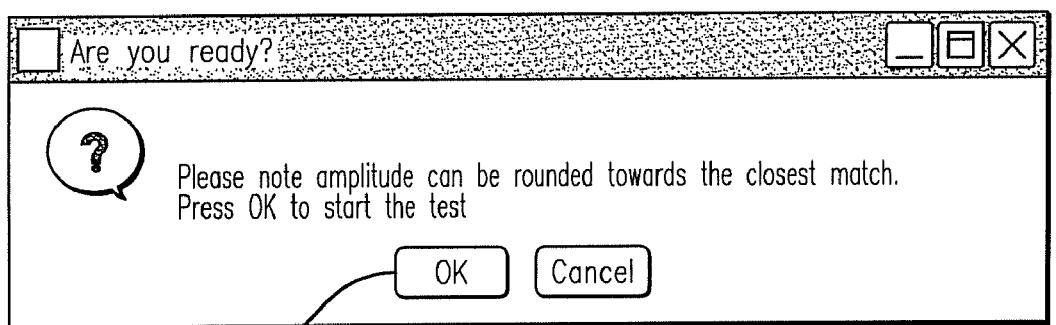

After the 'Run' button 195 or 'Show Waveform' button 194 are activated, the parameters may be checked against safety requirements of the system. If any of the parameters violates safety limits, a message box may be displayed and the experimenter will need to change the configuration parameters. Common errors may include broken/shorted electrodes and start amplitudes which exceed maximum charge per phase limit. For example, if there are any broken electrodes, the popup message shown in FIG. 37 may be displayed on the screen. If no safety violations are found once the broken electrodes have been removed or if no broken electrodes are found, the popup screen shown in FIG. 38 will appear after pressing 'Run' 195. If the requested pulse amplitude cannot be generated by the VPU 20, the closest value will automatically be used. The value will be displayed in the results section.

Figure 39:
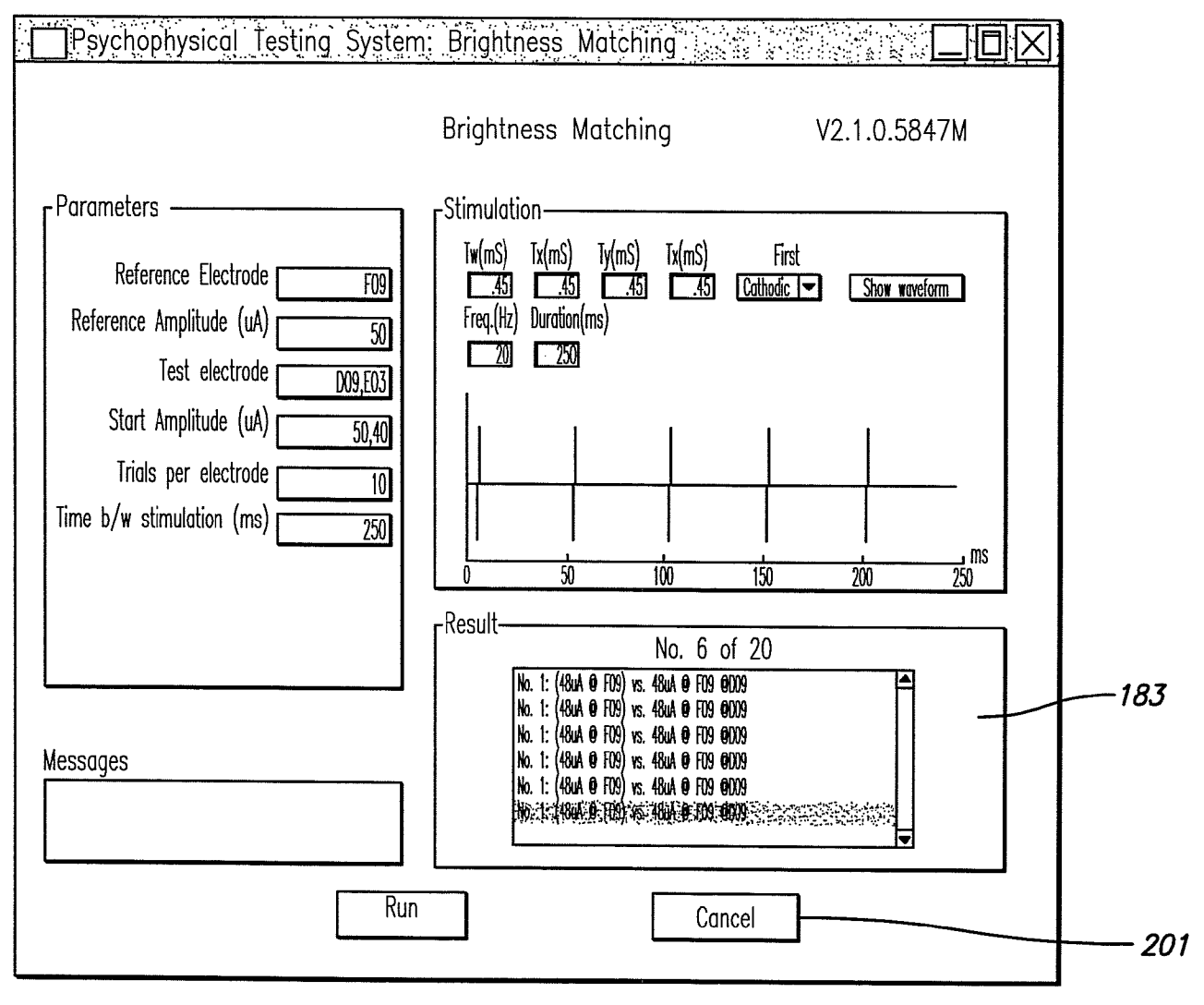

In this experiment, the subject is stimulated with two stimuli, one on the test electrode and one on the reference electrode. The order of the stimuli may be random. The subject may use the Tablet Patient Input Device 50 and presses the tablet keys to indicate which of the two intervals contains the brighter stimulus. The 'Results' panel 183 shown in FIG. 39 displays the amplitude values of the reference and test electrode for each trial. The program indicates which stimulus the subject selected by enclosing it in parentheses. If the subject indicates that the test electrode is brighter than the reference electrode, the system will decrease the test electrode amplitude and if the subject indicates that the standard (reference) electrode is brighter, the system will increase the test electrode amplitude. The presentation of the reference and test electrodes may occur in random order on a trial-by-trial basis.

The experiment ends once all of the trials have been completed. The Result panel 183 displays the total number of trials and the number of finished trials throughout the experiment. A 'Cancel' button 201 may be used to stop an experiment prior to the completion of all the trials.

Figure 40:
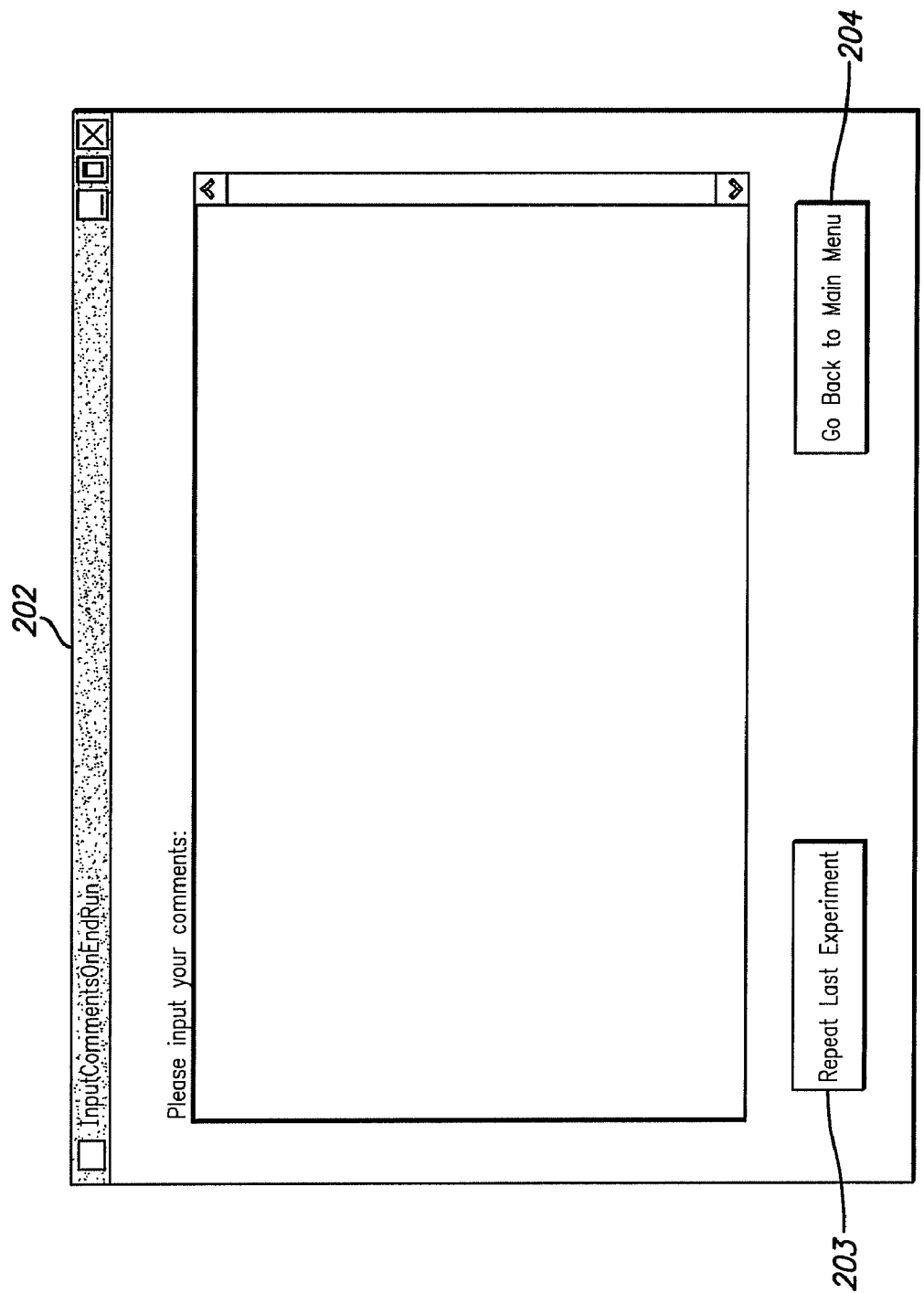
FIG. 40 shows an 'Input Your Comments' message box.

At the end of the experiment, the 'Comments' screen 202 shown in FIG. 40 may be used to allow the experimenter the option to comment. The 'Comments' screen 202 contains two buttons, 'Repeat Last Experiment' 203 and 'Go Back to Main Menu' 204. If 'Repeat Last Experiment' 203 is chosen, the experimenter will be returned to the main 'Brightness Matching' screen 178 of FIG. 35 with the Parameters from the last experiment and the experimenter can modify and repeat the experiment. If Go Back to Main Menu 204, is chosen, the experimenter will be returned to the main PTS menu 139 of FIG. 26.

Figure 41:
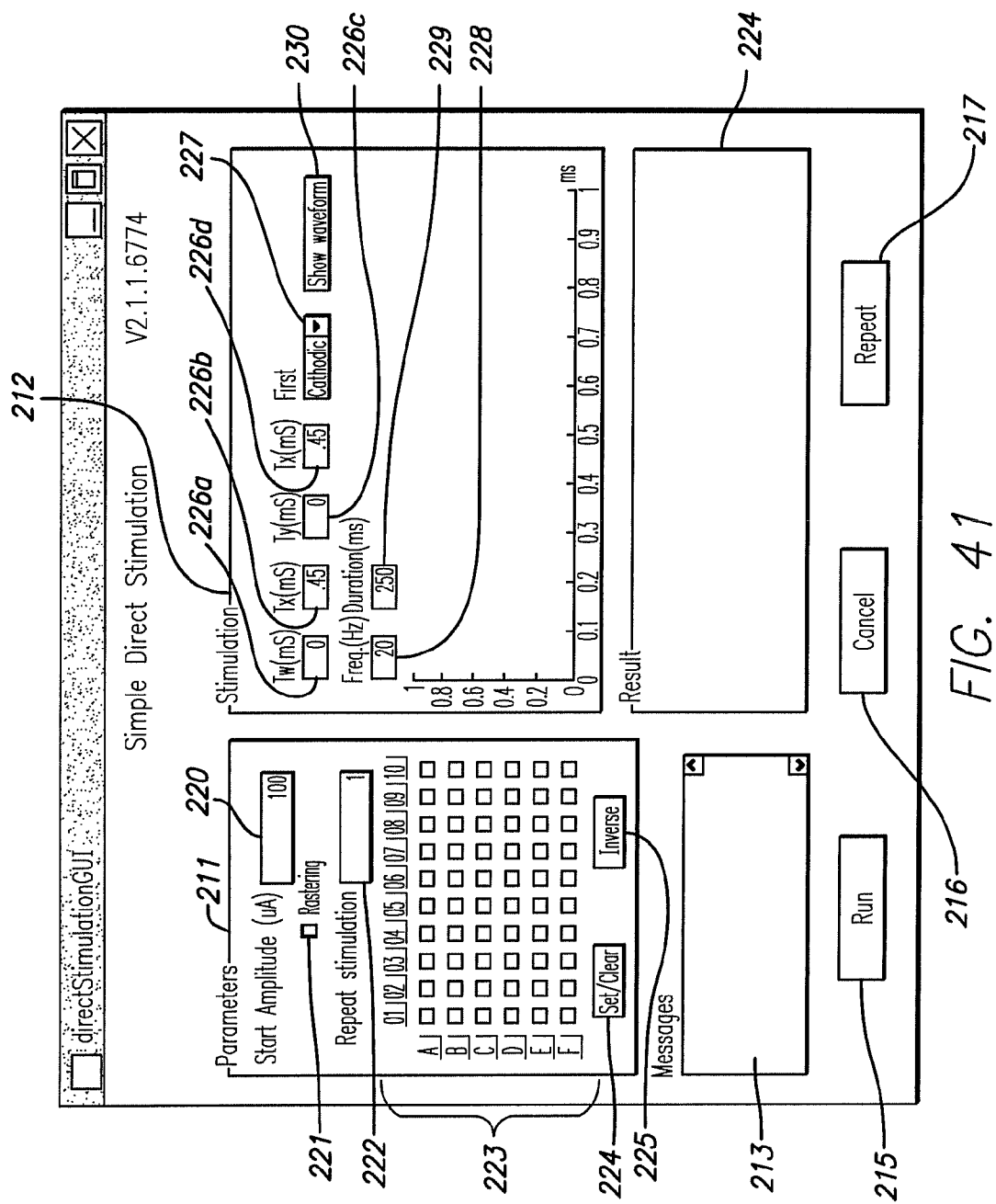
FIG. 41 shows a 'Simple Direct Stimulation' computer screen.
Figure 42:
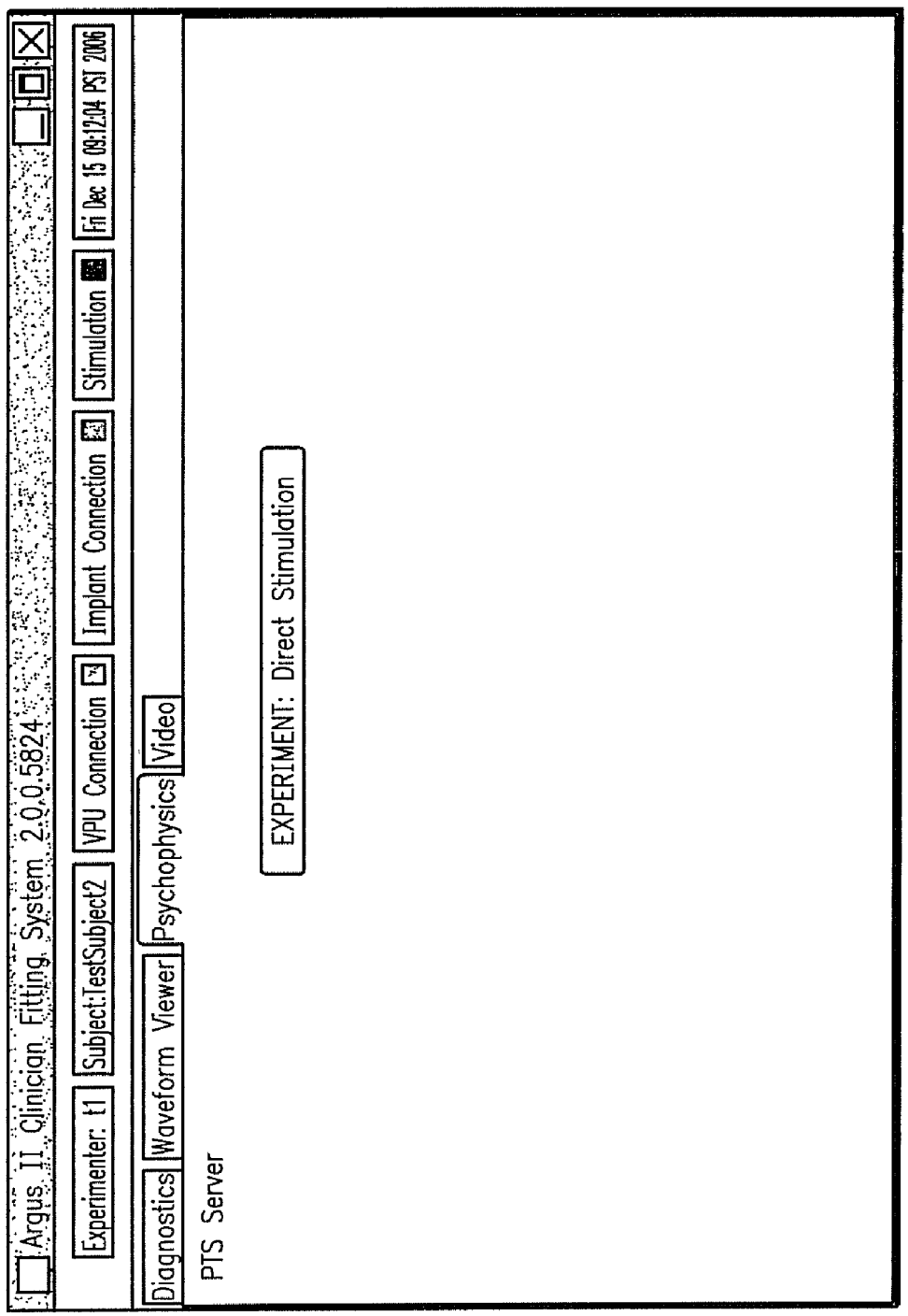
FIG. 42 shows an 'EXPERIMENT: direct stimulation' message box.

A 'Direct Stimulation' screen 210 shown in FIG. 41 appears when the 'Direct Stimulation' button 142 of FIG. 26 is selected from the PTS Main Menu Screen 139 of FIG. 26. The 'Direct Stimulation' screen 210 may also contain 1) 'Parameters' panel 211, 2) 'Stimulation' panel 212, 3) 'Message' panel 213, and 4) 'Result' panel 214. During a Direct Stimulation experiment, the PTS Server screen on the FS Laptop 10 may display "RUNNING: Direct Stimulation" as shown in FIG. 42.

Configuration parameters may be entered for the experiment as described below with reference to FIG. 41.

Starting stimulation amplitude(s) (μA) for each of the selected electrodes may be entered into a 'Start Amplitude' window 220 of the 'Parameters' panel 211. 'Rastering' 221 may be used to stagger the start times that electrodes are stimulated. When this option is not selected, all electrodes are stimulated simultaneously.

The number of times a stimulation will be repeated may be entered into a 'Repeat Stimulation' window 222 of the 'Parameters' panel 211. The time delay between successive repetitions may be approximately 0.5 seconds.

The electrodes to be stimulated can be selected from the 'Electrodes' windows 223 of the 'Parameters' panel 211. The electrodes may be individually selected by clicking individual boxes. Complete rows of electrodes may be selected or de-selected by clicking on the alphabetic button (A-F). Complete columns of electrodes may be selected or de-selected by clicking on the numeric button (01-10). All electrodes can be selected by using the 'Set/Clear' button 224. The inverse of the selected electrodes can be achieved by clicking on the 'Inverse' button 225.

A Pulse Width (ms) may be entered into windows 226*a-d* of the 'Stimulation' panel 212. A desired time between start of the effective stimulation window and initiation of the first phase may be entered into a Tw window 226*a*. The duration of the first phase may be entered into a Tx window 226*b*. The desired time between the end of the first phase and the beginning of the second phase may be entered into a Ty window 226*c*. Duration of the second phase may be entered into a Tz window 226*d*. FIG. 28 depicts a possible waveform of the numbers entered into windows 226*a-d*.

The frequency of how many times per second the waveform shown in FIG. 28 will be repeated may be entered into a 'Frequency' window 228 of the 'Stimulation' panel 212. A desired length of each stimulation in milliseconds (i.e. the length of stimulation at a given test amplitude) may be entered into a 'Duration' window 229 of the 'Stimulation' panel 212. Selection of whether the first phase is a negative (cathodic) current phase or a positive (anodic) current phase may be performed using the first window 227 of the 'Stimulation' panel 212. The 'Show Waveform' button 230 may be used to produce a graph that plots the waveform of the complete stimulus for a trial. The 'Run' button 215 may be used to proceed with the experiment.

Figure 43:
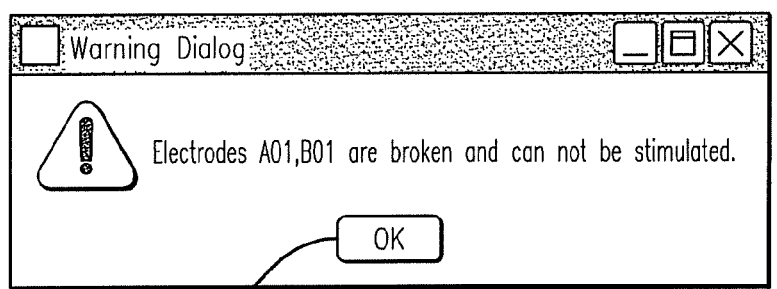
FIG. 43 shows a warning dialog box.

After the 'Run' button 215 or 'Show Waveform' button 230 are activated, the parameters may be checked against safety requirements of the system. If any of the parameters violates safety limits, a message box will be displayed and the experimenter will need to change the configuration parameters. Common errors may include broken/shorted electrodes, start amplitudes which exceed a maximum charge per phase limit (or the maximum total instantaneous current limit). For example, if there are any broken electrodes, the popup message shown in FIG. 43 may be displayed on the screen. While the experiment is running, the 'Result' screen 214 of FIG. 41 will indicate that stimulation is in progress. The 'Cancel' button 216 of FIG. 41 may be used to cancel Stimulation. A message (not shown) may appear indicating that stimulation was stopped by request.

Figure 44:
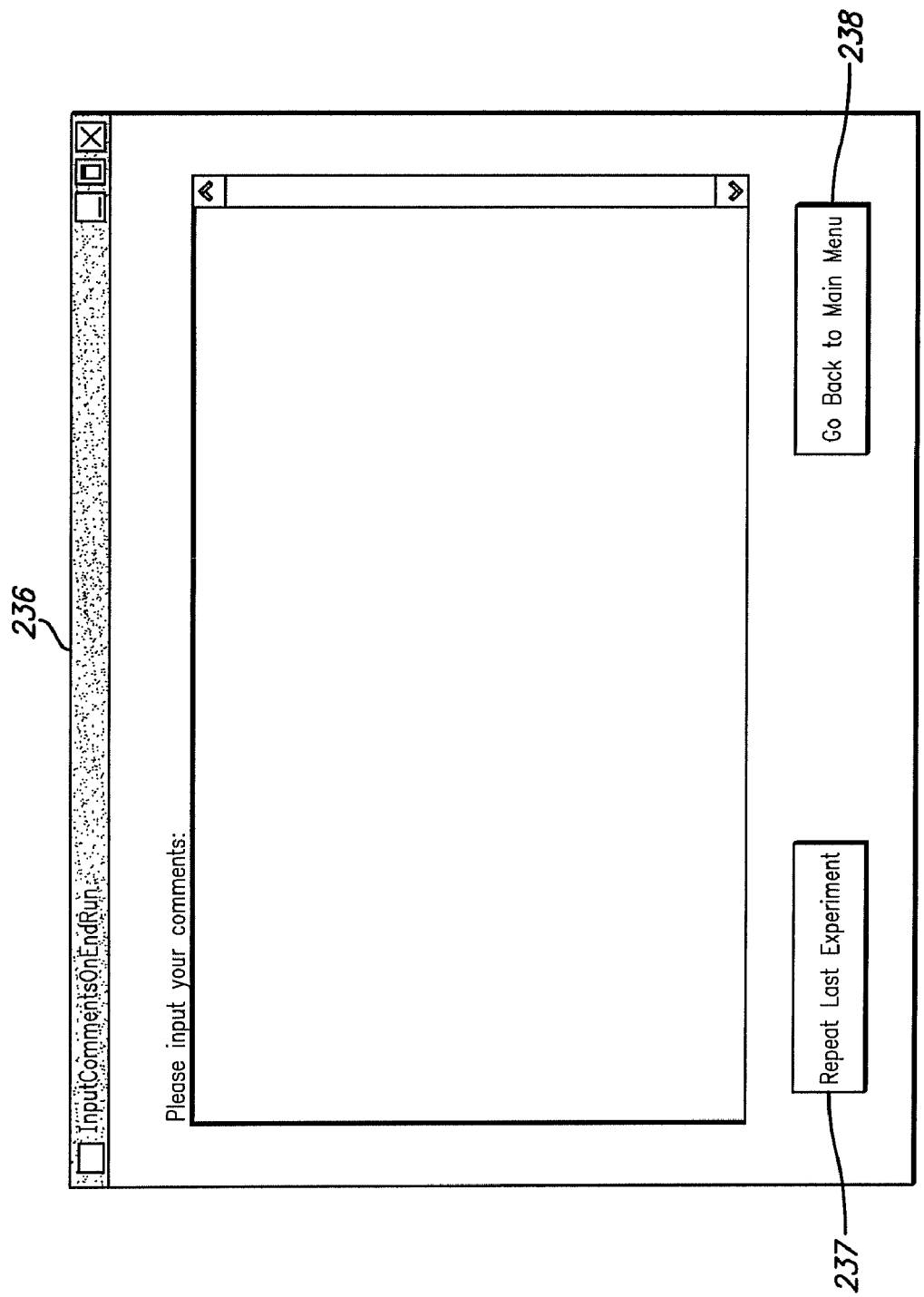
FIG. 44 shows an 'Input Your Comments' message box.

If stimulation has ended normally, a Comment screen 236 shown in FIG. 44 may be displayed. The Comment screen 236 contains two buttons, 'Repeat Last Experiment' 237 and 'Go Back to Main Menu' 238. If Repeat Last Experiment 237 is chosen, the experimenter will be returned to the main Direct Stimulation screen 210 with the Parameters from the last experiment and the experimenter can modify and repeat the experiment. If 'Go Back to Main Menu' 238, is chosen, the experimenter will be returned to the main PTS menu 139.

A Clinician-Designed Research Experiments module allows researchers to develop and execute their own custom-designed experiments for research purposes. Experimental psychophysical scripts are developed in MATLAB and are then executed within a MATLAB/PTS framework.

Accordingly, what has been shown is an improved method of stimulating neural tissue for improved response to brightness. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A computer-operated system for visual stimulation comprising a display component, the display component having a graphical user interface configured to display a visual representation of an image to a visual field of a patient, and wherein the graphical user interface is suitable for providing user feedback and suitable for supporting a method for fitting a visual prosthesis having a plurality of electrodes the graphical user interface comprising:
a first screen including means for selecting electrodes for visual stimulation, wherein selected electrodes for the visual stimulation create the visual representation displayed to the visual field of the patient; and
a second screen including a plurality of representations of threshold values within the visual representation of the visual field of the patient;
wherein the visual representation is displayed to the visual field of the patient and the plurality of electrodes are suitable to elicit perception of light.

2. The system of claim 1, wherein the first screen comprises an electrode window for selecting one or more electrodes to be activated.

3. The system of claim 1, wherein the first screen comprises a stimulation screen.

4. The system of claim 1, wherein the second screen provides one or more buttons that indicate which electrodes of the plurality of electrodes are activated.

5. A graphical user interface, the graphical user interface adapted to be displayed on a display component and used with a computer-operated system, the computer-operated system adapted for visual stimulation of a visual prosthesis having a plurality of electrodes, the graphical user interface configured to display a visual representation of an image to a visual field of a patient, the graphical user interface comprising:
a first screen, wherein the first screen comprises a plurality of stimulation selection buttons for visual stimulation, configured for selecting an electrode by pressing one of said plurality of stimulation selection buttons corresponding to the selected electrode;
a second screen including a plurality of representations of threshold values within the visual representation of the visual field of the patient;
wherein:
the visual representation is configured to be displayed to the visual field of the patient and is created by selecting the plurality of stimulation selection buttons based on the image, and
the plurality of electrodes are suitable to elicit perception of light.

6. The graphical user interface of claim 5, wherein the first screen is further configured to display a plurality of windows, and wherein the plurality of windows are configured for assigning values to stimulation parameters.

7. The graphical user interface of claim 6, wherein the stimulation parameters are at least one of stimulation amplitude of a particular electrode from the plurality of electrodes, time between successive stimulations by the particular electrode, and time differences between stimulations by one electrode in the plurality of electrodes and stimulation by another electrode in the plurality of electrodes.

8. The graphical user interface of claim 5, wherein the second screen is further configured to display a plurality of windows, and wherein the plurality of windows are configured for configuration of a pre-set experiment on the patient by use of the visual prosthesis.

9. The graphical user interface of claim 8, wherein the pre-set experiment is based on selection of at least one of: duration of time of an experiment, one or more electrodes from the plurality of electrodes to stimulate in the experiment, stimulation amplitude of the one or more electrodes at any given moment in time in the duration of time, and number of times to stimulate the one or more electrodes.

* * * * *